United States Patent [19]

Thominet et al.

[11] 4,186,135

[45] Jan. 29, 1980

[54] SUBSTITUTED 2,3-ALKYLENE BIS (OXY) BENZAMIDES AND DERIVATIVES AND METHOD OF PREPARATION

[75] Inventors: Michel Thominet; Gerard Bulteau, both of Paris; Jacques Acher, Itteville; Claude Collignon, Saint Remy les Chevreuse, all of France

[73] Assignee: Societe D'Etudes Scientifiques et Industrielles de L'ile-de-France, Paris, France

[21] Appl. No.: 821,123

[22] Filed: Aug. 2, 1977

[30] Foreign Application Priority Data

Aug. 4, 1976 [FR] France ............................... 76 23835

[51] Int. Cl.$^2$ .................... C07D 403/12; A61K 31/40
[52] U.S. Cl. ........................ 260/326.34; 260/239 BC; 260/239 A; 260/243.3; 260/245.5; 260/245.6; 548/256; 260/340.6; 424/250; 424/251; 424/248.5; 424/248.54; 424/256; 424/263; 424/267; 424/269; 424/270; 424/272; 424/273 R; 424/274; 424/278; 424/282; 544/148; 544/322; 544/328; 544/331; 544/377; 544/405; 546/133; 546/197; 546/270; 548/126; 548/336; 548/146; 548/218

[58] Field of Search ................................... 260/326.34

[56] References Cited

U.S. PATENT DOCUMENTS

| 2,688,826 | 8/1954 | Krimmel .......................... 260/326.34 |
| 2,725,386 | 11/1955 | Bovet et al. ..................... 260/326.34 |
| 3,124,598 | 3/1964 | Werner et al. ................... 260/326.34 |
| 3,378,066 | 2/1968 | Thominet et al. ............... 260/326.34 |
| 4,056,540 | 11/1977 | Buchanan ........................ 260/326.34 |

FOREIGN PATENT DOCUMENTS 755436  8/1956  United Kingdom ................ 260/326.34

*Primary Examiner*—Glennon H. Hollrah
*Assistant Examiner*—Mary Lee
*Attorney, Agent, or Firm*—John C. Smith, Jr.

[57] ABSTRACT

Novel substituted 2,3-alkylene bis (oxy) benzamides and derivatives thereof are disclosed. Also disclosed is a method for producing said compounds. The compounds have anxiolytic, psychostimulant, disinhibiting and thymoanaleptic properties useful therapeutically in the psychofunctional field, particularly in gastroenterology, cardiology, urology, rheumatology and gynaecology.

36 Claims, No Drawings

SUBSTITUTED 2,3-ALKYLENE BIS (OXY) BENZAMIDES AND DERIVATIVES AND METHOD OF PREPARATION

This invention relates to novel substituted 2,3-alkylene bis (oxy) benzamides, their pharmaceutically acceptable acid addition salts, their quarternary ammonium salts, their oxides, their dextrorotatory and levorotatory isomers and processes for their preparation. The invention also relates to the use of said compounds in pharmaceutical preparations for the treatment of psychofunctional disorders.

The structural formula of the substituted 2,3-alkylene bis (oxy) benzamides of the present invention is as follows:

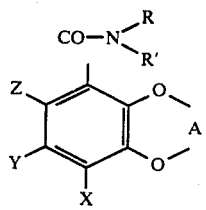

A is a $C_{1-3}$ alkylene chain which may or may not be substituted by a $C_{1-4}$ alkyl, a $C_{2-4}$ alkenyl, or a $C_{1-4}$ hydroxyalkyl group.

R is a hydrogen atom, a $C_{1-4}$ alkyl group or a radical having the general formula:

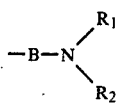

B is a single bond or a $C_{1-3}$ alkylene group which may or may not be substituted by a $C_{1-4}$ alkyl group or $C_{2-4}$ alkenyl group.

$R_1$ is a hydrogen atom, a $C_{1-4}$ alkyl, a $C_{2-4}$ alkenyl, a $C_{2-4}$ alkynyl or an alkyl group substituted, for example, by a hydroxy, mercapto, acyl, thioacyl, alkoxy, alkylthio, or a substituted or unsubstituted amino group. Also $R_1$ may be joined to B to form a saturated or unsaturated nitrogenous heterocycle such as azetidine, pyrrolidine, polyhydroazepine, pyrroline or polyhydropyridine.

$R_2$ is a hydrogen atom, a $C_{1-4}$ alkyl, a $C_{2-4}$ alkenyl, a $C_{2-4}$ alkynyl, or an alkyl group substituted, for example, by a hydroxy, mercapto, acyl, thioacyl, alkoxy, alkylthio or substituted or unsubstituted amino group, a substituted or unsubstituted, saturated or unsaturated heterocycle comprising at least one heteroatom such azetidine, pyrrolidine, piperidine, pyrimidine, pyrazine, furan, polyhydrofuran, pyran, polyhydropyran, quinuclidine, azabicycloalkane, diazabicycloalkane, or a phenyl, adamantyl, cycloalkyl, bicycloalkyl or cycloalkenyl group connected to the nitrogen atom of Formula II directly by a carbon atom of the ring or by means of a substituted or unsubstituted alkyl chain.

$R_2$ and $R_1$ can be connected together to form a heterocyclic ring which optionally may contain other heteroatoms. The resulting ring may, for example, be azetidine, pyrrolidine, piperidine, imidazolidine, piperazine, morpholine or thiazolidine. When the heterocyclic contains another nitrogen atom it can be substituted by any one of the following groups: $C_{1-4}$ alkyl, $C_{2-4}$ alkenyl, $C_{2-4}$ alkynyl, phenyl, benzyl, cycloalkyl, cycloalkenyl, cycloalkanealkyl, cycloalkenealkyl, adamantyl, bicycloalkyl, or alkyl substituted by a hydroxy, mercapto, acyl, thioacyl, alkoxy or alkylthio group.

R' is a hydrogen atom, $C_{1-4}$ alkyl, $C_{2-4}$ alkenyl, $C_{2-4}$ alkynyl, adamantyl, pyrimidinyl, pyrazinyl, diazepinyl, quinuclidinyl, azabicycloalkyl, diazabicycloalkyl, bicycloalkyl, substituted or unsubstituted phenyl or aralkyl group.

R' and B may be connected together to form a monoazotized heterocycle such as azetidine, pyrrolidine, piperidine, polyhydroazepine, azabicycloalkane, etc., which may or may not be substituted.

R' and $R_1$ may be joined together to form a saturated or unsaturated diazotized heterocycle such as piperazine, diazepine, pyrimidine, pyrazine, or diazabicycloalkane which may or may not be substituted.

X is a hydrogen or halogen atom or a hydroxy, amino (substituted or unsubstituted), $C_{1-4}$ alkoxy or $C_{1-4}$ alkyl group.

Y is a hydrogen or halogen atom or a hydroxy, amino (substituted or unsubstituted), nitro, $C_{1-4}$ alkoxy, $C_{1-4}$ alkylsulfonyl, adamantylsulfonyl or cycloalkylsulfonyl group. Also, Y may be a sulfonyl group substituted by an amino or a mono or disubstituted

wherein $R_3$ and $R_4$ may be identical or different and are hydrogen atoms or the following groups: $C_{1-4}$ alkyl, $C_{2-4}$ alkenyl, $C_{2-4}$ alkynyl, phenyl, benzyl, cycloalkyl, cycloalkanealkyl, cycloalkenealkyl, bycycloalkyl, adamantyl, pyrimidinyl, pyrazinyl or alkyl substituted by a hydroxy, mercapto, acyl, thioacyl, alkoxy or alkylthio group. Also $R_3$ and $R_4$ may form together with the nitrogen atom to which they are attached a heterocycle which may optionally contain another heteroatom.

Z is a hydrogen or halogen atom or a hydroxy, amino, substituted amino, nitro or $C_{1-4}$ alkoxy group.

X and Y or Y and Z may be connected together through a substituted or unsubstituted carbon chain or through other heteroatoms to form a cycle as for example a substituted or unsubstituted triazole, imidazole, oxazole, thiadizaole, pyrazine, piperazine, diazepine or one of their oxides.

The following definitions apply to the present specification:

alkyl $C_{1-4}$—methyl, ethyl, propyl, isopropyl, butyl, isobutyl and t-isobutyl alkylene $C_{1-3}$—methylene, ethylene and propylene alkenyl $C_{2-4}$—vinyl and allyl alkynyl $C_{2-4}$—ethinyl and propargyl alkoxy $C_{1-4}$—methoxy, ethoxy, propoxy, isopropoxy, butoxy, isobutoxy and t-butoxy aralkyl—benzyl, phenethyl unsubstituted or substituted by at least one halogen, alkoxy, alkyl, halomethyl and amino substituted phenyl—a phenyl ring substituted by at least one halogen atom, alkoxy, alkyl, halomethyl and amino halogen—chlorine, bromine, iodine and fluorine substituted amino—an amino group mono or d substituted by alkyl, acyl, aralkyl, furanyl, pyranyl and alkoxycarbonyl acyle—formyl, acetyl and phthaloyl The preferred values of X, Y and Z are follows:
X—hydrogen, alkoxy (primarily methoxy), nitro, halogen (primarily chlorine), amino and acylamino (primarily acetamino)
Y—hydrogen, halogen (primarily bromine and chlorine), amino, acylamino (primarily acetamino), alkylsulfonyl (primarily ethylsulfonyl) and a sulfonyl group substituted by
   an amino group
      an amino group, especially monosubstituted by an alkyl (primarily methyl), and an adamantyl group
      an amino group, especially disubstituted by an alkyl (primarily methyl or ethyl) group
Z—hydrogen, halogen, (primarily bromine and chlorine), nitro, acylamino (primarily acetamino) and amino.

The preferred substituents in the disubstituted compounds are:
[X—alkoxy (primarily methoxy) group
 Y—sulfonyl group substituted by an amino group
[X—acylamino (primarily acetamino) group
 Y—nitro group
X and Y can be joined together through a heteroatom (primarily nitrogen) to form a triazole cycle
X and Y—amino group
[X—halogen (primarily chlorine) atom
 Y—amino group
[X—amino group
 Y—acylamino (primarily acetamino) group
X and Y—acylamino (primarily acetamino) group
Y and Z—nitro group
Y and Z—acylamino (primarily acetamino) group
Y and Z—halogen (primarily bromine) atom
Y and Z—amino group
Y and Z can be joined together through a heteroatom (primarily nitrogen) to form a triazole cycle.

The preferred substituents in the trisubstituted compounds are:
[X—nitro group
 Y and Z—halogen (primarily chlorine and bromine) atom
[X—halogen (primarily chlorine and bromine) atom
 Y and Z—nitro group
[X—nitro group
 Y and Z—acylamino (primarily acetamino) group A is preferably an alkylene $C_{1-3}$ such as methylene, propylene and preferably ethylene. R' is preferably:
a hydrogen atom
an alkyl (primarily ethyl and butyl) group
an aralkyl group (primarily benzyl group which can be substituted with a halogen atom, preferably bromine or fluorine, or with a trifluoromethyl group).
an adamantyl or pyrimidinyl group
a saturated di-nitrogen heterocycle when linked to $R_1$ (preferably a piperazine ring which can be substituted).

R is preferably:
a hydrogen atom
an alkyl group (primarily ethyl)
a radical according to the Formula II in which the B is preferably
   a single bond
   an alkylen group (primarily ethylene and propylene)
   a nitrogen heterocycle when linked to $R_1$ such as defined hereafter.
$R_1$ is preferably
an alkyl group (primarily ethyl)
a saturated nitrogen heterocycle when linked to B (primarily pyrrolidine and piperidine groups)
a nitrogen heterocycle when linked to $R_2$
   primarily pyrrolidine and piperidine, or containing another heteroatom (primarily nitrogen), preferably a piperazine substituted with an alkyl group (primarily methyl or ethyl).
a saturated di-nitrogen heterocycle when linked to R', primarily a substituted piperazine group.

When, at the same time, $R_1$ is linked to $R_2$ such as to form a nitrogen heterocycle (primarily a pyrrolidine group) and $R_1$ is linked to R' such as to form a saturated di-nitrogen heterocycle (primarily a piperazine group), the whole constitutes a bicyclic radical, primarily a diazabicyclo nonane group.

The benzamide compounds of the present invention can be prepared by the reaction of a compound having the general formula:

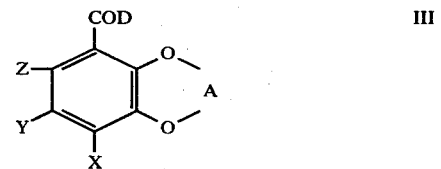

III wherein
A, X, Y and Z are as defined earlier, and
D is a hydroxy group, a halogen atom or an organic residue on an amine having the general formula:

IV wherein
R and R' are as defined earlier, or by the reaction of their reactive derivatives.

In the starting compound the organic residue comprises groups which are capable of forming reactive acid derivatives. These can be lower alkyl esters such as methyl, ethyl, propyl, isopropyl, butyl, isobutyl, t-butyl, pentyl, or isopentyl; reactive acid esters such as methoxymethyl ester, cyanomethyl ester, substituted or unsubstituted aromatic esters, or N-hydroxyimide esters; acid azides; acid hydrazides; symmetrical anhydrides; mixed anhydrides such as those formed from carboxylic acid esters and haloformic esters; azolides such as triazolides, tetrazolides and especially imidazolides, substituted $\Omega$-trihaloacetophenones; acid isothiocyanates; substituted $\alpha$-oxo benzeneacetonitriles; benzamides which are substituted on the ring, or other equivalents, or the compound having the general formula:

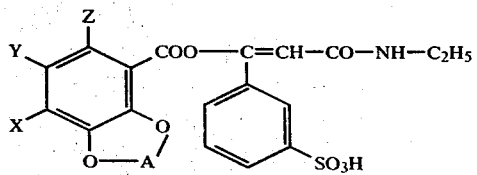

This compound may be formed from the acid and an isoxazolium salt. A, X, Y and Z are as defined above. However, the present invention is not limited to the reactive derivatives mentioned above.

According to the process of the present invention, the amine can react in the form of one of its reactive derivatives. By way of example, reference is made to the reaction products of the amine with phosphorus chlorides, phosphorus oxychloride, dialkyl, diaryl and orthophenylene chlorophosphites, alkyl or aryl dichlorophosphites or isothiocyanate of the amine or the symmetrical or assymetrical sulfamides of the amine, the corresponding symmetrical urea, the corresponding enamines or any other equivalent.

The above mentioned reactive derivatives can react with the acid in situ or after preliminary isolation. However, the invention is not limited to the reactive derivatives described above.

In addition, it is also possible to perform the reaction of the free acid and the free amine in the presence of a condensing agent, for example silicon tetrachloride, phosphoric anhydride or a carbodiimide such as dicyclohexyl carbodiimide or alkoxyacetylenes such as methoxy or ethoxyacetylene.

The following is a brief description of processes for preparing the benzamide compounds of the present invention:

The use of an acid halide is particularly suitable for
compounds which are unsubstituted on the benzene ring
compounds which are monosubstituted with a halogen atom, a nitro group, an alkylsulfonyl group, an adamantylsulfonyl group, a cycloalkylsulfonyl group or a sulfonyl radical substituted with either an amino group or an amino group mono or di-substituted with an alkyl group, an adamantyl group or a cycloalkyl group.

The use of alkyl esters, activated acid esters or aromatic esters is particularly suitable for
compounds having the benzene ring substituted with a hydroxy group, an amino group, an acylamino group, an alkylsulfonyl group, an adamantylsulfonyl group, a cycloalkylsulfonyl group or a sulfonyl group substituted with either an amino group or an amino group mono or di-substituted with an alkyl group, an adamantyl group or a cycloalkyl group.
compounds having two of X and Y or Y and Z radicals linked together so as to form a cycle.

The use of mixed anhydrides (formed in situ by reaction of the starting benzoic acid on haloformic esters, preferably chloroformic acid esters) is particularly suitable for compounds substituted with a nitro group, an acylamino group, or a sulfonyl group substituted with either an amino group or an amino group mono or di-substituted with an alkyl group, an adamantyl group or a cycloalkyl group.

The use of reactive derivatives of amines, preferably formed with phosphorus chlorides, and particularly the phosphorus trichloride, with alkyl and aryl chlorophosphites is particularly suitable for primary amines and especially aliphatic amines.

The amidification reaction of the invention can be carried out in the presence or in the absence of a solvent. Suitable solvents which are inert with respect to the amidification reaction are, for example, alcohols, polyols, benzene, toluene, dioxane, chloroform, diethylene glycol, dimethyl ether, and xylene. It is also possible to use as the solvent an excess of the amine used as the prime material. It may be preferable to heat the reaction mixture during the amidification operation, for example, up to the boiling temperature of the above mentioned solvents.

The compound produced by the process of the invention can react, if necessary, with pharmaceutically acceptable organic or inorganic acids such as hydrochloric acid, hydrobromic acid, sulfuric acid, phosphoric acid, oxalic acid, acetic acid, tartaric acid, citric acid and methane sulfonic acid to give acid addition salts.

The compound produced by the process of the invention can also react, if necessary, with alkyl halides or sulfates to give quaternary ammonium salts.

The compound can also be oxidized in a known manner, for instance by means of hydrogen peroxide and manganese dioxide, to obtain the corresponding N-oxide.

The substituted 2,3-alkylene bis (oxy) benzamides and derivatives thereof have been found to have anxiolytic, psychostimulant, disinhibiting and thymoanaleptic properties useful therapeutically in the psychofunctional field, particularly in gastro-enterology, cardiology, urology, rheumatology and gynaecology. The compounds of the present invention have been effective, for example, in the treatment of, anxiety, reactional depression, hot flushes resulting from menopause, cystitis, etc.

To further illustrate the features of the present invention, some embodiments will be described hereinafter, it being understood that these are not limiting as regards the mode of operation and the uses of the compounds.

EXAMPLE 1

N-(1-allyl-2-pyrrolidylmethyl)-7-methylsulfamoyl-1,4-benzodioxane-5-carboxamide 7-chlorosulfonyl-1,4-benzodioxane-5-carboxylic acid 670 g of chlorosulfonic acid were introduced into a balloon flask provided with a condenser and a thermometer. 173 g of 1,4-benzodioxane-5-carboxylic acid were added in portions with the temperature being maintained at 5°–10° C. The mixture was heated at 55° C. and then cooled and poured into ice. The precipitate was dried off, washed and dried again. 250 g of 7-chlorosulfonyl-1,4-benzodioxane-5-carboxylic acid were obtained (M.P.: 210°–215° C.; yield: 93.5%).

7-methylsulfamoyl-1,4-benzodioxane-5-carboxylic acid 139.5 g of a 40% methylamine aqueous solution and 139.5 cm$^3$ of water were introduced into a balloon flask provided with an agitator and a thermometer. Then, in portions, 250 g of 7-chlorosulfonyl-1,4-benzidioxane-5-carboxylic acid and a solution of 180 cm$^3$ of 30% soda lye in 180 cm$^3$ of water were added. The mixture was agitated and then poured into 2,200 cm$^3$ of water. The solution was filtered and then treated with 139 cm$^3$ of concentrated hydrochloric acid. The precipitate was dried off, washed and dried. 109.5 g of 7-methylsulfamoyl-1,4-benzodioxane-5-carboxylic acid were obtained (M.P.: 208°–209° C.; yield 80%).

7-methylsulfamoyl-1,4-benzodioxane-5-carbonyl chloride 176.5 g of thionyl chloride were introduced into a balloon flask provided with a condenser. Then, in portions, 135 g of 7-methylsulfamoyl-1,4-benzodioxane-5-carboxylic acid were added under heating at 40°–45° C. The mixture was heated under reflux and then treated with 250 cm$^3$ chloroform. The precipitate was dried off and washed with chloroform.

N-(1-allyl-2-pyrrolidylmethyl)-7-methylsulfamoyl-1,4-benzodioxane-5-carboxamide 69 g of 1-allyl-2-aminomethyl-pyrrolidine and 432 ml of chloroform were introduced into a 1-liter balloon flask provided with a thermometer and an agitator. 144 g of 7-methylsulfamoyl-1,4-benzodioxane-5-carbonyl chloride were added in portions with the temperature being maintained at 5°–10° C. Agitation of the mixture was continued for one hour and then the mixture was treated with 1,750 ml of water. After distillation of the chloroform the mixture was acidified to a pH value of 4 with 4 ml of 20% sulfuric acid and then filtered on carbon black. The solution of the sulfate formed was rendered alkaline with 60 ml of 20% ammonia. After crystallization, the base was dried off, washed with water and dried at 40° C. After recrystallization with acetonitrile 134 g of N-(1-allyl-2-pyrrolidylmethyl)-7-methyl-sulfamoyl-1,4-benzodioxane-5-carboxamide was produced (M.P.: 142°–143° C.; yield: 68.7%). The nuclear magnetic resonance spectra were found to be compatible with the proposed structure.

EXAMPLE 2

N-(1-ethyl-2-pyrrolidylmethyl)-7-sulfamoyl-1,4-benzodioxane-5-carboxamide

7-sulfamoyl-1,4-benzodioxane-5-carboxylic acid 209 g of 34% ammonia and 97 g of 7-chlorosulfonyl-1,4-benzodioxane-5-carboxylic acid were introduced into a balloon flask provided with an agitator and a thermometer at a temperature of 5°–10° C. The mixture was agitated at ambient temperature and then the precipitate was dissolved in 415 $cm^3$ of water. The solution was filtered and treated with 140 $cm^3$ of concentrated hydrochloric acid. The crystals were dried off, washed with water and dried. 78 g of 7-sulfamoyl-1,4-benzodioxane-5-carboxylic acid were obtained (M.P.: 272°–274° C.; yield: 87%).

Methyl-7-sulfamoyl-1,4-benzodioxane-5-carboxylate 429 g of methanol were introduced into a balloon flask provided with a condenser and then, under cooling, 54 g of 93% sulfuric acid and 111 g of 7-sulfamoyl-1,4-benzodioxane-5-carboxylic acid were added. The mixture was heated under reflux and then cooled. The crystals were dried off, washed with methanol and then treated with 500 $cm^3$ of water and 5 g of sodium carbonate. The precipitate was dried off, washed with water and dried. 95 g of methyl-7-sulfamoyl-1,4-benzodioxane-5-carboxylate were obtained (M.P.: 225°–226° C.; yield: 81%).

N-(1-ethyl-2-pyrrolidylmethyl-7-sulfamoyl-1,4-benzodioxane-5-carboxamide 145 g of methyl-7-sulfamoyl-1,4-benzodioxane-5-carboxylate, 48 g of water and 81.5 g of 1-ethyl-2-aminomethylpyrrolidine were introduced into a balloon flask provided with a reflux condenser and an agitator. The resulting suspension was heated on a water bath until a test sample was soluble in dilute acids. The reaction mixture was then treated with 1 liter of water and acidified with 70 ml of acetic acid. The acetate solution formed was filtered on carbon black and the base was precipitated with 20% ammonia. The crystals were dried off, washed with water and dried. The benzamide was purified by passage over hydrochloride (M.P.: 238°–240° C.). The base was reprecipitated with the addition of 20% ammonia. 120 g of N-(1-ethyl-2-pyrrolidylmethyl)-7-sulfamoyl-1,4-benzodioxane-5-carboxamide was produced (M.P. 160°–161° C.; yield: 61.5%). The nuclear magnetic resonance spectra were compatible with the proposed structure.

EXAMPLE 3

N-(1-methyl-2-pyrrolidylmethyl)-7-ethylsulfonyl-1,4-benzodioxane-5-carboxamide

7-mercapto-1,4-benzodioxane-5-carboxylic acid 243 g of 7-chlorosulfonyl-1,4-benzodioxane-5-carboxylic acid and 654 $cm^3$ of acetic acid were introduced into a balloon flask provided with an agitator and a condenser. The mixture was heated to 90° C. and then cooled to 45° C. 389 g of tin and 1,744 $cm^3$ of hydrochloric acid were then added. The mixture was heated to 55°–60° C., cooled and poured into water. The precipitate was dried off, washed and dried. 166 g of 7-mercapto-1,4-benzodioxane-5-carboxylic acid were obtained (M.P.: 191°–192° C.; yield: 90%).

7-ethylthio-1,4-benzodioxane-5-carboxylic acid 166 g of 7-mercapto-1,4-benzodioxane-5-carboxylic acid, 242 $cm^3$ of water, 216 $cm^3$ of soda lye and 181 g of ethylsulfate were introduced into a balloon flask provided with a condenser. The mixture was heated under reflux and then cooled. The solution was poured into 1.3 l of water, filtered and treated with 110 $cm^3$ of hydrochloric acid. The precipitate was dried off, washed with water and dried. 152 g of 7-ethylthio-1,4-benzodioxane-5-carboxylic acid were obtained (M.P.: 153°–154° C.; yield: 81%).

7-ethylsulfonyl-1,4-benzodioxane-5-carboxylic acid 152 g of 7-ethylthio-1,4-benzodioxane-5-carboxylic acid and 958 $cm^3$ of acetic acid were introduced into a balloon flask provided with a condenser. 398 $cm^3$ of hydrogen peroxide were then added and the mixture was heated. The crystals formed by cooling were dried off, washed and dried. 139 g of 7-ethylsulfonyl-1,4-benzodioxane-5-carboxylic acid were obtained (M.P.- 217°–218° C.; yield: 81%).

7-ethylsulfonyl-1,4-benzodioxane-5-carbonyl chloride 243 g of thionyl chloride, a few drops of dimethyl formamide and 139 g of 7-ethylsulfonyl-1,4-benzodioxane-5-carboxylic acid were introduced into a balloon flask provided with a condenser. The mixture was heated and then the thionyl chloride in excess was distilled off under vacuum. 148 g of 7-ethylsulfonyl-1,4-benzodioxane-5-carbonyl chloride were obtained (M.P.: 146°–147° C.; yield: 100%).

N-(1-methyl-2-pyrrolidylmethyl)-7-ethylsulfonyl-1,4-benzodioxane-5-carboxamide 59 g of 1-methyl-2-aminomethyl-pyrrolidine, 450 ml of chloroform and then, in portions, 150 g of 7-ethyl-sulfonyl-1,4-benzodioxane-5-carbonyl chloride were introduced at a temperature of 5°–10° C. into a balloon flask provided with an agitator and a thermometer. The mixture was then agitated for one hour at ambient temperature, and then 1,850 ml of water was added. After distillation of the chloroform the solution was filtered over carbon black and benzamide was precipitated by the addition of 65 ml of soda lye. The solid was dried off, washed with water and dried at 40° C. After recrystallization from absolute alcohol, 151 g of N-(1-methyl-2- pyrrolidylmethyl)-7-ethylsulfonyl-1,4-benzodioxane-5-carboxamide was obtained (M.P.: 140°–141° C.; yield: 80.5%). The structure was confirmed by nuclear magnetic resonance.

EXAMPLE 4

1-(2,3-ethylenedioxy-5-sulfamoylbenzoyl)-4-(2-pyrimidinyl)-piperazine 146 g of 7-sulfamoyl-1,4-benzodioxane-5-carboxylic acid, 300 ml of dioxane and 57 g of triethylamine were introduced into a 1-liter 3-neck flask provided with an agitator, a thermometer and an introduction funnel. The mixture was heated to 40°–50° C. and 80 ml of water was added. The solution was cooled to a temperature of from 5°–10° C. and 61.5 g of ethyl chloroformiate was added. Agitation of the mixture was maintained for one hour at 10° C. and 93 g of 1-(2-pyrimidinyl)-piperazine was added without the temperature rising above 15° C. Agitation of the mixture was continued for one hour at ambient temperature and then, after the addition of 1,500 ml of water, the mixture was rendered alkaline to a pH of 10 with ammonia. The crystals produced after distillation under vacuum of the solvents and cooling were dried off, washed with water, dried in a drying oven at 50° C. and then purified by treatment with 120 ml of chloroform. After filtration and drying, 92 g of 1-(2,3-ethylenedioxy-5-sulfamoylbenzoyl)-4-(2-pyrimidinyl)-piperazine was produced (M.P.: 239° C.; yield: 40.2%). The structure was confirmed by nuclear magnetic resonance.

EXAMPLE 5

N-(1-methyl-2-pyrrolidylmethyl)-7-dimethylsulfamoyl-1,4-benzodioxane-5-carboxamide 7-dimethylsulfamoyl-1,4-benzodioxane-5-carboxylic acid 500 cm³ of acetone and a solution of 99 g of dimethylamine in 250 cm³ of acetone were introduced into a balloon flask provided with an agitator and a thermometer. The mixture was cooled to 0° C. and then 139 g of 7-chlorosulfonyl-1,4-benzodioxane-5-carboxylic acid were introduced. The mixture was agitated at ambient temperature, the acetone distilled off and the residue dissolved in 1 liter of water. The solution was rendered alkaline, filtered and treated with 70 cm³ of hydrochloric acid. The precipitate was dried off, washed and dried. 128 g of 7-dimethylsulfamoyl-1,4-benzodioxane-5-carboxylic acid were obtained (M.P.: 220°–221° C.; yield: 89%).

7-dimethylsulfamoyl-1,4-benzodioxane-5-carbonyl chloride 190 g of thionyl chloride and 153 g of 7-dimethylsulfamoyl-1,4-benzodioxane-5-carboxylic acid were introduced into a balloon flask provided with a condenser. The mixture was heated and then the excess thionyl chloride was distilled off. 163 g of 7-dimethylsulfamoyl-1,4-benzodioxane-5-carbonyl chloride were obtained (M.P.: 160°–162° C.; yield: 100%).

N-(1-methyl-2-pyrrolidylmethyl)-7-dimethylsulfamoyl-1,4-benzodioxane-5-carboxamide 61 g of 1-methyl-2-aminomethyl-pyrrolidine and 560 ml of chloroform were introduced into a balloon flask provided with an agitator and a thermometer, and then with the temperature maintained at from 0°–5° C. 163 g of 7-dimethyl-sulfamoyl-1,4-benzodioxane-5-carbonyl chloride was introduced. The mixture was agitated for one hour, allowing the temperature to rise, and then 1 liter of water was added. After distillation of the chloroform the solution was filtered and the carboxamide was precipitated by adding 30% soda lye. The crystals produced were filtered, washed with water and dried. After recrystallization from absolute alcohol, 157 g of N-(1-methyl-2-pyrrolidylmethyl)-8-dimethylsulfamoyl-1,4-benzodioxane-5-carboxamide was obtained (M.P.: 165°–166° C.; yield: 76.9%). The nuclear magnetic resonance spectra were compatible with the proposed structure.

EXAMPLE 6

N-(1'benzyl-2-pyrrolidylmethyl)-1,4-benzodioxane-5-carboxamide phosphate 440 ml of chloroform and 110 g of 1-benzyl-2-aminomethylpyrrolidine were introduced into a balloon flask provided with an agitator and a thermometer, and then, at a temperature of from 5°–10° C., 110 g of 1,4-benzodioxane-5-carbonyl chloride was added. After agitation of the mixture and addition of 3 liters of water, chloroform was removed.

The solution was treated with ammonia and then the precipitate was extracted with methylene chloride. The organic solution was dried and then the solvent was removed. The resulting compound dissolved in absolute ethanol was treated with 30 ml of 85% phosphoric acid. The precipitate formed was dried off, washed with ethanol and dried. 153 g of N-(1-benzyl-2-pyrrolidylmethyl)-1,4-benzodioxane-5-carboxamide phosphate was produced (M.P.: 165° C.; yield: 61%).

EXAMPLE 7

N-(1-allyl-2-pyrrolidylmethyl)-7-sulfamoyl-1,4-benzodioxane-5-carboxamide 145 g of methyl-7-sulfamoyl-1,4-benzodioxane-5-carboxylate, 48 g of water and 89 g of 1-allyl-2-aminomethylpyrrolidine were introduced into a balloon flask provided with a condenser. The mixture was heated on a water bath until a test sample was soluble in dilute acids and then 1 liter of water was added. The precipitated carboxamide was redissolved by acetate formation. The solution formed was filtered on carbon black and then the base was precipitated by the addition of 20% ammonia. The resulting crystals were dried off, washed with water, dried and purified by passing over hydrochloride (M.P.: 228°–230° C.) followed by transformation into a base by treatment with 20% ammonia. 131 g of N-(1-allyl-2-pyrrolidylmethyl)-7-sulfamoyl-1,4-benzodioxane-5-carboxamide was produced (M.P.: 143°–144° C.; yield: 64.8%). The structure was confirmed by nuclear magnetic resonance.

EXAMPLE 8

N-(1-ethyl-2-pyrrolidylmethyl)-7-methylsulfamoyl-1,4-benzodioxane-5-carboxamide

Methyl-7-methylsulfamoyl-1,4-benzodioxane-5-carboxylate 750 ml of methanol were introduced into a balloon flask provided with a condenser. Then, under cooling, 273 g of concentrated sulfuric acid and 160 g of 7-methylsulfamoyl-1,4-benzodioxane-5-carboxylic acid were added. The mixture was heated under eflux, cooled and poured into water and sodium carbonate. The precipitate was dried off, washed and dried. 143 g of methyl-7-methylsulfamoyl-1,4-benzodioxane-5-carboxylate were obtained (M.P.: 159°–160° C.; yield: 85%).

N-(1-ethyl-2-pyrrolidylmethyl)-7-methylsulfamoyl-1,4-benzodioxane-5-carboxamide 137 g of methyl-7-methylsulfamoyl-1,4-benzodioxane-5-carboxylate, 43 g of water and 73 g of 1-ethyl-2-aminomethylpyrrolidine were introduced into a balloon flask provided with an agitator and a reflux condenser. The mixture was heated on a water bath until a test sample was totally soluble in dilute acids. The carboxamide produced by cooling was purified by passing it over acetate and then treated with 100 ml of acetic acid in 950 ml of water. After the resulting solution was filtered on carbon black, the base was precipitated by the addition of 20% ammonia. The resulting crystals were dried off, washed with water, dried and purified by recrystallization from boiling isopropyl alcohol. 121 g of N-(1-ethyl-2-pyrrolidylmethyl)-7-methylsulfamoyl-1,4-benzodioxane-5-carboxamide was produced (M.P.: 139°–140° C.; yield: 66.2%). The structure was confirmed by nuclear magnetic resonance analysis. The corresponding hydrochloride was produced by treatment of the carboxamide with hydrochloric acid (specific gravity: 1.18; M.P.: 186°–188° C.).

EXAMPLE 9

N-(1-ethyl-2-pyrrolidylmethyl)-2,3-methylenedioxybenzamide

In a similar manner, 34.9 g of ethyl 2,3-methylenedioxy benzolate was reacted with 24.2 g of 1-ethyl-2-aminomethylpyrrolidine, to give, after treatment and purification, 28.3 g of N-(1-ethyl-2-pyrrolidylmethyl)-2,3-methylenedioxy benzamide. The nuclear magnectic resonance spectra were compatible with the expected structure.

EXAMPLE 10

Levorotatory N-(1-ethyl-2-pyrrolidylmethyl)-7-ethylsulfonyl-1,4-benzodioxane-5-carboxamide 65 g of levorotatory-1-ethyl-2-aminomethyl-pyrrolidine was dissolved in 430 ml of chloroform in a balloon flask provided with an agitator and a thermometer. The resulting solution was cooled to 5° C. and then 148 g of finely pulverized 7-ethylsulfonyl-1,4-benzodioxane-5-carbonyl chloride was added with the temperature being maintained at from 5°–10° C. At the end of the operation of introducing this substance the mixture was agitated for one hour and then treated with 1 liter of water. After distillation of the chloroform the solution was filtered on carbon black and the base was precipitated with an excess of 30% soda. The resulting crystals were dried off, washed with water, dried and recrystallized from isopropyl alcohol. 151.5 g of levorotatory N-(1-ethyl-2-pyrrolidylmethyl)-7-ethylsulfonyl-1,4-benzodioxane-5-carboxamide was produced (M.P.: 111°–112° C.; yield: 77.7%); $(\alpha)_D^{20} = -54.2°$ (in 5% solution in dimethylformamide).

EXAMPLE 11

Dextrorotatory N-(1-ethyl-2-pyrrolidylmethyl)-7-ethylsulfonyl-1,4-benzodioxane-5-carboxamide In a similar manner 64.5 g of dextrorotary-1-ethyl-2-aminomethylpyrrolidine was reacted with 146 g of 7-ethylsulfonyl-1,4-benzodioxane-5-carbonyl chloride to give, after treatment and purification, 133.5 g of dextrorotatory N-(1-ethyl-2-pyrrolidylmethyl)-7-ethylsulfonyl-1,4-benzodioxane-5-carboxamide (M.P.: 111°–122° C.; yield: 69.8%); $(\alpha)_D^{20} = 55.5°$ (in 5% solution in dimethylformamide).

EXAMPLE 12

N-(1-ethyl-2-pyrrolidylmethyl-7-ethylsulfonyl-1,4-benzodioxane-5-carboxamide hydrochloride In a similar manner 58 g of 1-ethyl-2-aminomethylpyrrolidine was reacted with 131 g of 7-ethylsulfonyl-1,4-benzodioxane-5-carbonyl chloride to give, after treatment and purification, 103.5 g of N-(1-ethyl-2-pyrrolidylmethyl)-7-ethylsulfonyl-1,4-benzodioxane-5-carboxamide (M.P.: 118°–119° C.; yield: 60.2%). 100 g of the base produced was dissolved in 220 ml of acetone and then the solution was filtered on carbon black and a solution of 9.5 g of hydrochloric acid in acetone was added. The resulting hydrochloride crystals were dried off, washed with acetone and then dried. 96 g of N-(1-ethyl-2-pyrrolidylmethyl)-7-ethylsulfonyl-1,4-benzodioxane-5-carboxamide hydrochloride was produced (M.P.: 148°–150° C.; yield: 88.2%).

EXAMPLE 13

N-(1-methyl-2-pyrrolidylmethyl)-7-sulfamoyl-1,4-benzodioxane-5-carboxamide 131 g of methyl-7-sulfamoyl-1,4-benzodioxane-5-carboxylate, 43 g of water and 66 g of 1-methyl-2-aminomethylpyrrolidine were introduced into a balloon flask provided with a reflux condenser. The mixture was heated on a water bath until a test sample was totally soluble in dilute acids. The carboxamide produced by cooling was purified by treatment with a solution of 50 ml of acetic acid in 1250 ml of water. After the resulting solution was filtered on carbon black, the base was precipitated by the addition of 20% ammonia. The resulting crystals were dried off, washed with water, dried and purified by recrystallization from boiling methyl alcohol. 119.5 g of N-(1-methyl-2-pyrrolidylmethyl)-7-sulfamoyl-1,4-benzodioxane-5-carboxamide was produced (M.P.: 187°–188° C.; yield: 70.1%).

EXAMPLE 14

N-(1-allyl-2-pyrrolidylmethyl)-7-ethylsulfonyl-1,4-benzodioxane-5-carboxamide hydrochloride 58 g of 1-allyl-2-aminomethyl-pyrrolidine and 360 ml of chloroform were introduced into a balloon flask provided with an agitator and a thermometer and then, with the temperature being maintained at 5°–10° C., 120 g of 7-ethylsulfonyl-1,4-benzodioxane-5-carbonyl chloride was added. After agitation of the mixture and the addition of a liter of water, the chloroform was distilled. The resulting solution was filtered on carbon black and then the base was precipitated by the addition of 40 ml of 30% soda lye. The resulting crystals were dried off, washed with water and then dried. 152 g of N-(1-allyl-2-pyrrolidylmethyl)-7-ethylsulfonyl-1,4-benzodioxane-5-carboxamide was produced (M.P.: 78°–80° C.; yield: 93.4%). 146 g of the resulting base was dissolved hot in 290 ml of absolute alcohol, and then the solution was filtered on carbon black and acidified by the addition of a solution of 13.5 g of hydrochloric acid in 100 ml of absolute alcohol. After cooling the crystals formed were dried off, washed with absolute alcohol and dried and then purified by recrystallization from absolute alcohol. 119.5 g of N-(1-allyl-2-pyrrolidylmethyl)-7-ethylsulfonyl-1,4-benzodioxane-5-carboxamide hydrochloride was produced (M.P.: 138°–140° C.; yield: 75%).

EXAMPLE 15

N-(1-ethyl-2-pyrrolidylmethyl)-2H-3,4-dihydro-1,5-benzodioxepine-6-carboxamide phosphate Methyl-2H-3,4-dihydro-1,5-benzodioxepine-6-carboxylate 111 g of methyl-2,3-dihydroxybenzoate, 660 cm$^3$ of methylethylcetone, 167 g of 1,3-dibromopropane and 10 g of sodium iodide were introduced into a balloon flask provided with an agitator and a thermometer. The mixture was heated to 40° C. and then 182 g of potassium carbonate were added. The mixture was heated under reflux and 2 liters of water were added. The oily phase was decanted, extracted with ether and the solution was washed with 10% soda and dried. The ether was removed. By distillation under vacuum, 86.5 g of methyl-2H-3,4-dihydro-1,5-benzodioxepine-6-carboxylate were obtained (Boiling Point: 166°–176° C. under 8 mm/Hg; yield: 63%).

2H-3,4-dihydro-1,5-benzodioxepine-6-carboxylic acid 160 g of methyl-2H-3,4-dihydro-1,5-benzodioxepine-6-carboxylate and 388 cm$^3$ of soda were introduced into a balloon flask provided with a condenser. The mixture was heated under reflux and then poured into 1 liter of water and treated with 5 g of sodium metabisulfite. The solution was filtered and treated with 77 cm$^3$ of concentrated hydrochloric acid. The precipitate was drained off, washed with water and dried. 120 g of 2H-3,4-dihydro-1,5-benzodioxepine-6-carboxylic acid were obtained (M.P.: 65°–67° C.; yield: 80.5%).

2H-3,4-dihydro-1,5-benzodioxepine-6-carbonyl-chloride 246 g of thionyl chloride and 134 g of 2H-3,4-dihydro-1,5-benzodioxepine-6-carboxylic acid were introduced into a balloon flask provided with a condenser. The mixture was heated under reflux and then the thionyl chloride was distilled off under vacuum. 147 g of 2H-3,4-dihydro-1,5-benzodioxepine-6-carbonyl chloride were obtained (M.P.: 35°–37° C.; yield: 100%).

N-(1-ethyl-2-pyrrolidylmethyl)-2H-3,4-dihydro-1,5-benzodioxepine-6-carboxamide 92 g of 1-ethyl-2-aminomethylpyrrolidine and 458 ml of chloroform were introduced into a balloon flask provided with an agitator and a thermometer and then, with the temperature being kept at from 5°–10° C., 152 g of 2H-3,4-dihydro-1,5-benzodioxepine-6-carbonyl chloride was added. After agitation for one hour with the temperature being allowed to rise, 1,450 ml of water was added and then the chloroform was distilled. The solution was filtered over carbon black and the base was precipitated by the addition of 75 ml of 20% ammonia. The crystals formed were dried off, washed with water and dried. 191 g of N-(1-ethyl-2-pyrrolidylmethyl)-2H-3,4-dihydro-1,5-benzodioxepine-6-carboxamide monohydrate was produced (M.P.: 51°–52° C.; yield: 82.4%). 173.5 g of the compound produced was dissolved in 750 ml of absolute alcohol. The solution was filtered over carbon black and then a solution of 62 g of 85% phosphoric acid in 100 ml of absolute alcohol was added. The crystals formed were dried off, washed with absolute alcohol and dried and then recrystallized from alcohol. 198 g of N-(1-ethyl-2-pyrrolidylmethyl)-2H-3,4-dihydro-1,5-benzodioxepine-6-carboxamide phosphate was produced (M.P.: 189°–190° C.; yield: 92%).

EXAMPLE 16

N-(1-methyl-2-pyrrolidylmethyl)-7-methylsulfamoyl-1,4-benzodioxane-5-carboxamide 169 g of methyl-7-methylsulfamoyl-1,4-benzodioxane-5-carboxylate, 53 ml of water and 81 g of 1-methyl-2-aminomethylpyrrolidine were introduced into a balloon flask provided with a reflux condenser. The mixture was heated on a water bath until a test sample was totally soluble in dilute acids. The resulting crystals were dissolved in a solution of 50 ml of acetic acid in 1,250 ml of water and then the solution was filtered over carbon black and the base was reprecipitated by the addition of 100 ml of 20% ml of 20% ammonia. The crystals were dried off, washed with water and dried. 182 g of N-(1-methyl-2-pyrrolidylmethyl)-1,4-benzodioxane-5-carboxamide was produced (M.P.: 189°–190° C.; yield 83.6%).

EXAMPLE 17

N-(diethylaminoethyl)-1,4-benzodioxane-5-carboxamide hydrochloride 21 g of diethylaminoethylamine and 85 ml of acetone were introduced into a balloon flask provided with an agitator and a thermometer. The mixture was cooled to 0° C. and then 36 g of 1,4-benzodioxane-5-carbonyl chloride were added. The crystals formed at ambient temperature were dried off, washed with acetone, dried and purified by recrystallization from isopropyl alcohol. 36.5 g of N-(diethylaminoethyl)-1,4-benzodioxane-5-carboxamide hydrochloride were obtained (M.P.: 120° C.; yield: 64%).

EXAMPLE 18

N-(1-ethyl-2-pyrrolidylmethyl)-7-ethylsulfonyl-1,4-benzodioxane-5-carboxamide 13 g of 7-ethylsulfonyl-1,4-benzodioxane-5-carboxylic acid, 300 ml of tetrahydrofuran and 13 g of carbonyldiimidazole were introduced into a balloon flask provided with an agitator, a thermometer and a condenser. The mixture was agitated at ambient temperature and then 9.5 g of 1-ethyl-2-aminomethylpyrrolidine was added. Agitation was maintained at ambient temperature and then the solvent was evaporated under vacuum. The crystals produced were washed with water and then dried. 14 g of N-(1-ethyl-2-pyrrolidylmethyl)-7-ethylsulfonyl-1,4-benzodioxane-5-carboxamide was produced (M.P.: 118°–119° C.; yield: 73.8%)

EXAMPLE 19

N-(1-methyl-2-pyrrolidylmethyl)-7-dimethylsulfamoyl-1,4-benzodioxane-5-carboxamide A solution of 6 g of 1-methyl-2-aminomethylpyrrolidine in pyridine was produced and then, dropwise, with agitation and with the temperature being kept at from 0°–5° C., a solution of 3.5 g of phosphorus trichloride in 20 ml of pyridine were introduced into a balloon flask provided with an agitator, a thermometer and a condenser. Agitation was maintained at a temperature of from 0°–5° C. and then at ambient temperature. 14.5 g of 7-dimethylsulfamoyl-1,4-benzodioxane-5-carboxylic acid was then added. The mixture was heated with agitation. After the mixture had been cooled and the solvent removed the residue was dissolved in chloroform and then the solution was washed with aqueous sodium carbonate and dried on anhydrous magnesium sulfate. After concentration under reduced pressure, 12.5 g of N-(1-methyl-2-pyrrolidylmethyl)-7-dimethylsulfamoyl-1,4-benzodioxane-5-carboxamide was produced (M.P.: 165°–166° C.; yield: 64.5%).

EXAMPLE 20

N-(1-cyclohexyl-3-pyrrolidyl)-7-methylsulfamoyl-1,4-benzodioxane-5-carboxamide 84 g of 1-cyclohexyl-3-aminopyrrolidine, 430 ml of chloroform and 146 g of 7-methylsulfamoyl-1,4-benzodioxane-5-carbonyl chloride were introduced into a balloon flask provided with an agitator and a thermometer. After agitation of the mixture, the base was extracted with methylene chloride and then the solvent was evaporated. The crystals formed were dissolved in boiling absolute alcohol and the resulting solution was filtered on carbon black. The crystals produced after cooling were dissolved in a solution of acetic acid in water and then the solution was filtered over carbon black and the base was reprecipitated by the addition of 20% ammonia. 129.5 g of N-(1-cyclohexyl-3-pyrrolidyl)-7-methylsulfamoyl-1,4-benzodioxane-5-carboxamide was produced (M.P.: 160°–161° C.; yield: 61.2%).

EXAMPLE 21

N-(1-ethyl-2-pyrrolidylmethyl)-7-dimethylsulfamoyl-1,4-benzodioxane-5-carboxamide 64 g of 1-ethyl-2-aminomethyl-pyrrolidine and 530 ml of chloroform were introduced into a balloon flask provided with an agitator and a thermometer, and then with the temperature being maintained at from 0°–5° C. 153 g of 7-dimethyl-sulfamoyl-1,4-benzodioxane-5-carbonyl chloride was added. The mixture was agitated for an hour allowing the temperature to rise and then 1 liter of water was added. After distillation of the chloroform the solution was filtered and the carboxamide was precipitated by the addition of 30% soda lye. The crystals produced were filtered, washed with water and dried. After recrystallization from absolute alcohol 144.5 g of N-(1-ethyl-2-pyrrolidylmethyl)-7-dimethylsulfamoyl-1,4-benzodioxane-5-carboxamide was obtained (M.P.: 146°–148° C.; yield: 72.8%).

EXAMPLE 22

Dextrorotatory-N-(1-ethyl-2-pyrrolidylmethyl)-7-methylsulfamoyl-1,4-benzodioxane-5-carboxamide 82 g of dextrorotatory 1-ethyl-2-aminomethylpyrrolidine, 600 ccm of chloroform and, gradually, at a temperature of from 5°–10° C., 200 g of 7-methylsulfamoyl-1,4-benzodioxane-5-carbonyl chloride were introduced into a balloon flask with an agitator and a thermometer. After the addition of a liter of water chloroform was distilled and then the remaining solution was filtered. The base was precipitated by the addition of 60 cm³ of 20% ammonia. The crystals formed were dried off, washed with water and then dried. 162 g of dextrorotatory N-(1-ethyl-2-pyrrolidylmethyl)-7-methylsulfamoyl-1,4-benzodioxane-5-carboxamide was produced (M.P.: 136°–137° C.; yield: 66%).

EXAMPLE 23

Levorotatory-N-(1-ethyl-2-pyrrolidylmethyl)-7-methylsulfamoyl-1,4-benzodioxane-5-carboxamide In a similar manner to that of the above example, 82 g of levorotatory 1-ethyl-2-aminomethyl-pyrrolidine was reacted with 195 g of 7-methylsulfamoyl-1,4-benzodioxane-5-carbonyl chloride to give 151 g of levorotatory-N-(1-ethyl-2-pyrrolidylmethyl)-7-methylsulfamoyl-1,4-benzodioxane-5-carboxamide (M.P.: 136°–137° C.; yield: 62%).

EXAMPLE 24

Levorotatory-N-(1-allyl-2-pyrrolidylmethyl)-7-methylsulfamoyl-1,4-benzodioxane-5-carboxamide 85 g of levorotatory 1-allyl-2-aminomethyl-pyrrolidine, 610 cm³ of chloroform, and gradually, 178 g of 7-methylsulfamoyl-1,4-benzodioxane-5-carbonyl chloride at a temperature of from 5°–10° C. were introduced into a balloon flask provided with an agitator and a thermometer. After agitation of the mixture 1.2 liters of water were added and then chloroform was distilled. The remaining solution was filtered and then the base was precipitated with 70 cm³ of 20% ammonia. The crystals formed were dried off and washed with water. After recrystallization from ethyl acetate, 117 g of levorotatory-N-(1-allyl-2-pyrrolidylmethyl)-7-methylsulfamoyl-1,4-benzodioxane-5-carboxamide was produced (M.P.: 101°–102° C.; yield: 49%).

EXAMPLE 25

Dextrorotatory-N-(1-allyl-2-pyrrolidylmethyl)-7-methylsulfamoyl-1,4-bennzodioxane-5-carboxamide In a similar manner to the above example, 84 g of dextrorotatory 1-allyl-2-aminomethyl-pyrrolidine was reacted with 175 g of 7-methylsulfamoyl-1,4-benzodioxane-5-carbonyl chloride to give, after purification, 125 g of dextrorotatory-N-(1-allyl-2-pyrrolidylmethyl)-7-methylsulfamoyl-1,4-benzodioxane-5-carboxamide (M.P.: 104°–105° C.; yield: 52.6%).

EXAMPLE 26

Dextrorotatory-N-(1-methyl-2-pyrrolidylmethyl)-7-methylsulfamoyl-1,4-benzodioxane-5-carboxamide 61 g of dextrorotatory 1-methyl-2-aminomethylpyrrolidine, 465 ccm of chloroform and, in portions, 155 g of 7-methylsulfamoyl-1,4-benzodioxane-5-carbonyl chloride, with the temperature being maintained at 5°–10° C., were introduced into a balloon flask provided with an agitator and a thermometer. After agitation of the mixture and the addition of 1,850 cm³ of water, chloroform was distilled and the remaining solution was filtered. The base was precipitated by the addition of 65 cm³ of 20% ammonia. The crystals formed were dried off, washed and dried. 154 g of dextrorotatory-N-(1-methyl-2-pyrrolidylmethyl)-7-methylsulfamoyl-1,4-benzodioxane-5-carboxamide was produced (M.P.: 187°–188° C.; yield: 78.5%).

EXAMPLE 27

Levorotatory-N-(1-methyl-2-pyrrolidylmethyl)-7-methylsulfamoyl-1,4-benzodioxane-5-carboxamide In a similar manner to that of the above example, 71 g of levorotatory 1-methyl-2-aminomethyl-pyrrolidine was reacted with 180.5 g of 7-methylsulfamoyl-1,4-benzodioxane-5-carbonyl chloride to give 175 g of levorotatory-N-(1-methyl-2-pyrrolidylmethyl)-7-methylsulfamoyl-1,4-benzodioxane-5-carboxamide (M.P.: 187°–187.5° C.; yield: 77%).

EXAMPLE 28

N-(1-ethyl-2-pyrrolidylmethyl)-8-methylsulfamoyl-2H-3,4-dihydro-1,5-benzodioxepine-6-carboxamide 8-chlorosulfonyl-2H-3,4-dihydro-1,5-benzodioxepine-6-carboxylic acid 1,092 cm³ of chlorosulfonic acid were introduced into a balloon flask provided with an agitator, a condenser and a thermometer. Then, in portions, 106 g of 2H-3,4-dihydro-1,5-benzodioxepine-6-carboxylic acid were added, with the temperature being maintained at from 5°–10° C. The mixture was agitated at ambient temperature and then poured on ice. The crystals were dried off, washed with water and dried. 146 g of 8-chlorosulfonyl-2H-3,4-dihydro-1,5-benzodioxepine-6-carboxylic acid were obtained (M.P.: 114°–115° C.; yield: 91%).

8-methylsulfamoyl-2H-3,4-dihydro-1,5-benzodioxepine-6-carboxylic acid 233 g of a methylamine aqueous solution were introduced into a balloon flask provided with an agitator and a thermometer and then, in portions, 146 g of 8-chlorosulfonyl-2H-3,4-dihydro-1,5-benzodioxepine-6-carboxylic acid were added, with the temperature being maintained at from 5°–10° C. The mixture was agitated and the precipitate was then dissolved in water. The solution was filtered and treated with 150 cm³ of concentrated hydrochloric acid. The crystals were dried off, washed and dried. 112 g of 8-methylsulfamoyl-2H-3,4-dihydro-1,5-benzodioxepine-6-carboxylic acid were obtained (M.P.: 145°–146° C.; yield: 78%).

8-methylsulfamoyl-2H-3,4-dihydro-1,5-benzodioxepine-6-carbonyl chloride 220 g of thionyl chloride and 177 g of 8-methylsulfamoyl-2H-3,4-dihydro-1,5-benzodioxepine-6-carboxylic acid were introduced into a balloon flask provided with a condenser. The mixture was heated and then the thionyl chloride was distilled off under vacuum. 188 g of 8-methylsulfamoyl-2H-3,4-dihydro-1,5-benzodioxepine-6-carbonyl chloride were obtained (M.P.: 93°–94° C.; yield: 100%).

N-(1-ethyl-2-pyrrolidylmethyl)-8-methylsulfamoyl-2H-3,4-dihydro-1,5-benzodioxepine-6-carboxamide 79 g of 1-ethyl-2-aminomethyl-pyrrolidine, 750 cm³ of methyl ethyl ketone and, gradually, 188 g of 8-methylsulfamoyl-2H-3,4-dihydro-1,5-benzodioxepine-6-carbonyl chloride, with the temperature being maintained at from 5°–10° C., were introduced into a balloon flask provided with an agitator and a thermometer. The hydrochloride precipitate was dried off, washed with methyl ethyl ketone and then dried. After recrystallization from methyl alcohol the hydrochloride was dissolved in 850 cm³ of water. The solution was filtered and then the base was precipitated by the addition of 60 cm³ of 20% ammonia. The crystals formed were dried off, washed with water and then dried. 180 g of N-(1-ethyl-2-pyrrolidylmethyl)-8-methylsulfamoyl-2H-3,4-dihydro-1,5-benzodioxepine-6-carboxamide was produced (M.P.: 144°–145° C.; yield: 63.8%).

EXAMPLE 29

N-(1-ethyl-2-pyrrolidylmethyl)-2,3-methylenedioxybenzamide hydrochloride 134 g of 1-ethyl-2-aminomethyl-pyrrolidine, 950 cm³ of chloroform and, gradually, 183 g of 2,3-methylenedioxyl benzoyl chloride, with the temperature being maintained at from 5°–10° C., were introduced into a balloon flask provided with an agitator and a thermometer. After the addition of 1 liter of water, chloroform was distilled and then the remaining solution was filtered. After the addition of 120 cm³ of 20% ammonia and extraction with ether, the ethereal solution was dried on potassium carbonate and then the ether was distilled. The base produced was dissolved in 30 cm³ of acetone and then a solution of 34 g of hydrochloric acid in 330 cm³ of acetone was added. The hydrochloride precipitate was dried, washed with acetone and then dried. After recrystallization from isopropyl alcohol, 154 g of N-(1-ethyl-2-pyrrolidylmethyl)-2,3-methylenedioxybenzamide hydrochloride was produced (M.P.: 127.5°–128.5° C.; yield: 49.7%).

EXAMPLE 30

4-(1,4-benzodioxane-7-ethylsulfonyl-5-carbonyl)-1,4-diazabicyclo-(4-3-0)-nonane 41.5 g of 1,4-diazabicyclo-(4-3-0)-nonane and 300 ml of chloroform were introduced into a 1 liter balloon flask. The mixture was cooled to 5° and then 87 g of 7-ethylsulfonyl-1,4-benzodioxane-5-carbonyl chloride was added in small amounts. After agitation of the mixture at ambient temperature, 5 g of acticarbon was added. After filtration and removal of the chloroform the oily residue was dissolved in 200 ml of water and then 30 ml of 20% ammonia was added. The resulting residue was dried and then recrystallized from acetone. 40 g of 4-(1,4-benzodioxane-7-ethylsulfonyl-5-carbonyl)-1,4-diazabicyclo-(4-3-0)-nonane was produced (M.P.: 147° C.; yield: 35%).

EXAMPLE 31

5-[(4-methyl-1-piperazinyl)-carbonyl]-7-nitro-1,4-benzodioxane-hydrochloride 7-nitro-1,4-benzodioxane-5-carboxylic acid 160 ml of acetic acid, 160 ml of acetic anhydride and 100 g of 1,4-benzodioxane-5-carboxylic acid were introduced into a balloon flask provided with an agitator and a thermometer. The mixture was heated and a solution of 40 ml of nitric acid in 40 ml of acetic acid was added. The mixture was agitated at 40°–45° C. and then cooled. The crystals were dried off, washed and dried. 34 g of 7-nitro-1,4-benzodioxane-5-carboxylic acid were obtained (M.P.: 246° C.; yield: 27%).

5-[(4-methyl-1-piperazinyl)-carbonyl]-7-nitro-1,4-benzodioxane-hydrochloride 22 ml of water, 22.5 g of 7-nitro-1,4-benzodioxane-5-carboxylic acid, 65 ml of acetone and 10.5 g of triethylamine were introduced into a 250 ml balloon flask provided with an agitator and a thermometer. The mixture was cooled to 10° C. and then 14 g of isobutyl chloroformiate was added. The mixture was agitated and the temperature allowed to rise. The oily compound formed was cooled to 10° C., 11 g of N-methyl piperazine was added and then the mixture was agitated, allowing the temperature to rise. The crystals formed were washed with water. 20.5 g of 5-[(4-methyl-1-piperazinyl)-carbonyl]-7-nitro-1,4-benzodioxane was produced (M.P.: 218° C.; yield: 66.7%).

The 20.5 g of base produced was treated by a solution of 7 ml of hydrochloric acid (specific gravity=1.18) in 100 ml of water. The crystals formed by cooling were washed with water and then dried. 20.5 g of 5-[(4-methyl-1-piperazinyl)-carbonyl]-7-nitro-1,4-benzodioxane hydrochloride was produced (M.P. 250° C.; yield: 89.4%).

EXAMPLE 32

5-[(4-methyl-1-piperazinyl)-carbonyl]-7-[(1-adamantyl)-sulfamoyl]-1,4-benzodioxane hydrochloride 7-(1-adamantyl)-sulfamoyl-1,4-benzodioxane-5-carboxylic acid 187.5 g of adamantylamine hydrochloride, 500 ml of soda and 1,000 ml of triethylamine were introduced into a balloon flask provided with an agitator and a thermometer. 280 g of 7-chlorosulfonyl-1,4-benzodioxane-5-carboxylic acid was then added at a temperature below 15° C. The mixture was agitated at ambient temperature and treated with 1.5 liters of methylene chloride. The organic phase was separated and the solvent removed. The residue was treated with 7,200 ml of water and 150 ml of hydrochloric acid and then the precipitate was dissolved in 1,200 ml of water and 120 ml of soda. The solution was filtered and treated with 150 ml of hydrochloric acid. The crystals were dried off, washed and dried. 200 g of 7-(1-adamantyl)-sulfamoyl-1,4-benzodioxane-5-carboxylic acid were obtained (M.P.: 205° C.; yield: 51%).

5-[(4-methyl-1-piperazinyl)-carbonyl]-7-[(1-adamantyl)-sulfamoyl]-1,4-benzodioxane hydrochloride 500 ml of dioxane and 49 g of 7-(1-adamantyl)-sulfamoyl-1,4-benzodioxane-5-carboxylic acid were introduced into a 1 liter balloon flask provided with an agitator and a thermometer. After agitation of the mixture, 12.5 g of triethylamine was added and then, in small amounts, 17 g of isobutyl chloroformiate was added. After agitation of the mixture at a temperature of 20° C. a solution of 14 g of N-methyl piperazine in 50 ml of dioxane was introduced. The mixture was agitated and then cooled. The triethylamine hydrochloride formed was removed by filtration and the filtrate was concentrated under vacuum and then dissolved in 300 ml of water. 15 ml of hydrochloric acid was added and then the solution was treated with 20 ml of ammonia. The product formed was dissolved in 150 ml of boiling ethanol and the solution was filtered hot. A solution of hydrochloric acid in absolute ethanol was added to the filtrate until the pH was 1. The crystals formed were dried off, washed with ethanol and dried. 37 g of 5-[(4-methyl-1-piperazinyl)-carbonyl]-7-[(1-adamantyl)-sulfamoyl]-1,4-benzodioxane hydrochloride was produced (M.P.: 260° C.; yield: 58%).

EXAMPLE 33

N-(piperidinoethyl)-7-chloro-1,4-benzodioxane-5-carboxamide hydrochloride 7-amino-1,4-benzodioxane-5-carboxylic acid 56 g of 7-nitro-1,4-benzodioxane-5-carboxylic acid, 560 ml of absolute ethanol and Raney nickel were introduced into an autoclave and then hydrogen under a pressure of 65 kg/cm$^2$ was introduced while heating. The mixture was then agitated at 60° C. and treated with a solution of 50 ml of soda lye in 450 ml of water. The solution was filtered and treated with 50 ml of hydrochloric acid. The precipitate was dried off, washed with water and dried. 36.5 g of 7-amino-1,4-benzodioxane-5-carboxylic acid were obtained (M.P.: 220° C.; yield: 75%).

7-chloro-1,4-benzodioxane-5-carboxylic acid 49 g of 7-amino-1,4-benzodioxane-5-carboxylic acid, 200 ml of water and 50 ml of hydrochloric acid were introduced into a balloon flask provided with an agitator and a thermometer. The mixture was cooled to 5° C. and then a solution of 17.5 g of sodium nitrite in 38 ml of water was added. The suspension was then poured into a solution of 20 g of cuprous chloride in 75 ml of hydrochloric acid. The precipitate was dried off, washed and dissolved in a solution of 42 g of sodium bicarbonate in 420 ml of water. The solution was filtered and treated with 100 ml of hydrochloric acid. 50 g of 7-chloro-1,4-benzodioxane-5-carboxylic acid was produced (M.P.: 180° C.; yield: 92.7%).

7-chloro-1,4-benzodioxane-5-carbonyl chloride 32.2 g of 7-chloro-1,4-benzodioxane-5-carboxylic acid and 64 ml of thionyl chloride were introduced into a balloon flask provided with an agitator, a thermometer and a condenser. The mixture was heated under reflux and then the thionyl chloride in excess was distilled off under vacuum. 35 g of 7-chloro-1,4-benzodioxane-5-carbonyl chloride were obtained (M.P.: 140° C.; yield: 100%).

N-(piperidino ethyl)-7-chloro-1,4-benzodioxane-5-carboxamide hydrochloride 150 ml of methyl ethyl ketone and 22 g of N-(aminoethyl)-piperidine were introduced into a 500 ml balloon flask provided with an agitator and a thermometer. The mixture was cooled and then a suspension of 35 g of 7-chloro-1,4-benzodioxane-5-carbonyl chloride in 200 ml of methyl ethyl ketone was added at a temperature of from 15°-20° C. After agitation the crystals formed were dried off and then washed with methyl ethyl ketone. 35 g of N-[piperidino ethyl]-7-chloro-1,4-benzodioxane-5-carboxamide hydrochloride was produced (M.P.: 192° C.; yield: 64.5%).

EXAMPLE 34

N-(butyl)-7-[(1-adamantyl)-sulfamoyl]-1,4-benzodioxane-5-carboxamide 500 ml of dioxane, 50 ml of water, 49 g of 7-[(1-adamantyl)-sulfamoyl]-1,4-benzodioxane-5-carboxylic acid and 12.5 g of triethylamine were introduced into a 2-liter balloon flask provided with an agitator and a thermometer. The solution was agitated at ambient temperature and then 17 g of isobutyl chloroformiate was added. The mixture was agitated and then 10 g of butylamine was introduced. After agitation of the mixture dioxane was removed. The residue was dissolved in 200 ml of hot water. The crystals formed by cooling were washed with water, dried and redissolved in 250 ml of acetone at boiling temperature. The solution was filtered hot. The crystals formed by cooling were dried off, washed and dried. 26 g of N-(butyl)-7-[(1-adamantyl)-sulfamoyl]-1,4-benzodioxane-5-carboxamide was produced (M.P. 147° C.; yield: 46.4%).

EXAMPLE 35

N-(1-ethyl-2-pyrrolidylmethyl)-8-methoxy-1,4-benzodioxane-5-carboxamide oxalate 8-methoxy-1,4-benzodioxane-5-carboxylic acid 171.5 g of 2,3-dihydroxy-4-methoxy benzoic acid, 515 cm$^3$ of alcohol, 280 cm$^3$ of soda lye and 175 g of ethylene bromide were introduced into a balloon flask provided with an agitator, a thermometer and an inlet pipe for nitrogen. The mixture was heated under reflux and then cooled and poured into 2.8 liters of water. The solution was filtered and treated with 85 cm$^3$ of concentrated hydrochloric acid. The precipitate was dried off, washed and dried. After recrystallization in dimethylformamide, 110 g of 8-methoxy-1,4-benzodioxane-5-carboxylic acid were obtained (M.P.: 224°–226° C.; yield: 57%).

8-methoxy-1,4-benzodioxane-5-carbonyl chloride 391 g of thionyl chloride and 138 g of 8-methoxy-1,4-benzodioxane-5-carboxylic acid were introduced into a balloon flask provided with a condenser. The mixture was heated to 50°–55° C. and the excess thionyl chloride was distilled off under vacuum. 151 g of 8-methoxy-1,4-benzodioxane-5-carbonyl chloride were obtained (yield: 100%).

N-(1-ethyl-2-pyrrolidylmethyl)-8-methoxy-1,4-benzodioxane-5-carboxamide oxalate 87 g of 1-ethyl-2-aminomethyl pyrrolidine and 775 cm$^3$ of methyl ethyl ketone were introduced into a balloon flask provided with an agitator and a thermometer and then, in portions, 155 g of 8-methoxy-1,4-benzodioxane-5-carbonyl chloride was added, with the temperature being maintained at from 5°–10° C. After agitation the mixture was dissolved with 1,500 cm$^3$ of water and then the methyl ethyl ketone was distilled. The remaining solution was filtered and then treated with sodium hydroxide. The oil was decanted and then extracted with methylene chloride. The solution was dried on potassium carbonate and then the methylene chloride was distilled under vacuum. 224.5 g of N-(1-ethyl-2-pyrrolidylmethyl)-8-methoxy-1,4-benzodioxane-5-carboxamide was produced. 197.5 g of the base produced was dissolved in 760 cm$^3$ of absolute alcohol, and then 67 g of oxalic acid in solution in 195 cm$^3$ of absolute alcohol was added. The crystals formed were dried off, washed with absolute alcohol and then dried. 208.5 g of N-(1-ethyl-2-pyrrolidylmethyl)-8-methoxy-1,4-benzodioxane-5-carboxamide oxalate was produced (M.P. 129°–130° C.; yield: 82%).

EXAMPLE 36

N-(1-ethyl-2-pyrrolidylmethyl)-8-methoxy-7-sulfamoyl-1,4-benzodioxane-5-carboxamide 8-methoxy-7-chlorosulfonyl-1,4-benzodioxane-5-carboxylic acid 1045 cm$^3$ of chlorosulfonic acid were introduced into a balloon flask provided with an agitator, a thermometer and a condenser and then, in portions, 110 g of 8-methoxy-1,4-benzodioxane-5-carboxylic acid were added with the temperature being maintained at from 5°–10° C. The mixture was agitated at ambient temperature and then poured on ice. The precipitate was dried off, washed and dried. 159 g of 8-methoxy-7-chlorosulfonyl-1,4-benzodioxane-5-carboxylic acid were obtained (yield: 98%).

8-methoxy-7-sulfamoyl-1,4-benzodioxane-5-carboxylic acid 300 g of 34% ammonia were introduced into a balloon flask provided with an agitator and a thermometer and then 159 g of 8-methoxy-7-chlorosulfonyl-1,4-benzodioxane-5-carboxylic acid were added in portions, the temperature being maintained at from 0°–5° C. The mixture was agitated and then the precipitate was dissolved in water. The solution was filtered and treated with 280 cm$^3$ of concentrated hydrochloric acid. The precipitate was dried off, washed and dried. 118 g of 8-methoxy-7-sulfamoyl-1,4-benzodioxane-5-carboxylic acid were obtained (M.P.: 247°–248° C.; yield: 82%).

Methyl-8-methoxy-7-sulfamoyl-1,4-benzodioxane-5-carboxylate 396 g of methanol were introduced into a balloon flask provided with a condenser and then 51 g of sulfuric acid and 114.5 g of 8-methoxy-7-sulfamoyl-1,4-benzodioxane-5-carboxylic acid were added while cooling. The mixture was heated under reflux and then poured into 485 cm$^3$ of water and 40 g of sodium carbonate. The precipitate was dried off, washed and dried. 110.5 g of methyl-8-methoxy-7-sulfamoyl-1,4-benzodioxane-5-carboxylate were obtained (M.P.: 202°–203° C.; yield: 92%).

N-(1-ethyl-2-pyrrolidylmethyl)-8-methoxy-7-sulfamoyl-1,4-benzodioxane-5-carboxamide 150 g of methyl-8-methoxy-7-sulfamoyl-1,4-benzodioxane-5-carboxylate and 750 cm$^3$ of ethylene glycol were introduced into a balloon flask. After dissolution, 127 g of 1-ethyl-2-aminomethylpyrrolidine was added and the mixture was heated at 50° C. The resulting solution was dissolved with 2 liters of water and acidified by means of 120 cm$^3$ of acetic acid. The precipitate formed was dried off, washed with water and then dried. The precipitate was then redissolved in 915 cm$^3$ of hot water. The solution was filtered and then the base was precipitated with ammonia. The precipitate was dried off, washed with water and then dried. 144 g of N-(1-ethyl-2-pyrrolidyl-methyl)-8-methoxy-7-sulfamoyl-1,4-benzodioxane-5-carboxamide was produced (M.P.: 110°–115° C.; yield: 73%).

EXAMPLE 37

4-(1,4-benzodioxane-5-carbonyl)-1,4-diazabicyclo-(4-3-0)-nonane 63 g of 1,4-diaza-bicyclo-(4-3-0)-nonane and 400 ml of chloroform were introduced into a 1-liter balloon flask provided with an agitator and a thermometer and then, in portions, 50 g of 1,4-benzodioxane-5-carbonyl chloride was added, with the temperature being maintained at 10° C. The mixture was then agitated at ambient temperature and then 1 liter of water was added. After the addition of acetic acid to give a pH of 4 and the addition of carbon black and filtration, the product was precipitated with ammonia. After extraction with methylene chloride the solution was dried and then filtered. The solvent was removed under vacuum and the resulting product was purified by recrystallization from ethanol. 50 g of 4-(1,4-benzodioxane-5-carbonyl)-1,4-diazabicyclo-(4-3-0)-nonane was produced (M.P.: 128° C.; yield: 69%).

EXAMPLE 38

N-(benzyl)-7-diethylsulfamoyl-1,4-benzodioxane-5-carboxamide 7-diethylsulfamoyl-1,4-benzodioxane-5-carboxylic acid 200 ml of water, 100 ml of diethylamine and 200 ml of triethylamine were introduced into a balloon flask provided with an agitator and a thermometer and then 140 g of 7-chlorosulfonyl-1,4-benzodioxane-5-carboxylic acid were added in portions, the temperature being maintained at from 20°–30° C. The mixture was agitated at ambient temperature and then 500 ml of water were added. The solution was filtered and treated with 300 ml of hydrochloric acid. The precipitate was dried off, washed and dried. 117 g of 7-diethylsulfamoyl-1,4-benzodioxane-5-carboxylic acid were obtained (M.P.: 149° C.; yield: 74%).

N-(benzyl)-7-diethylsulfamoyl-1,4-benzodioxane-5-carboxamide 37.8 g of 7-diethylsulfamoyl-1,4-benzodioxane-5-carboxylic acid, 40 ml of water, 12.5 g of triethylamine and 120 ml of acetone were introduced into a balloon flask provided with an agitator and a thermometer. The mixture was cooled to about 10°–15° C. and then 17.2 g of isobutyl chloroformiate was added. After the addition, at a temperature of from 15°–20° C., of 14.1 g of benzylamine and agitation of the mixture the crystals formed were dried off, washed with water and then purified by recrystallization from ethanol. 33 g of N-(benzyl)-7-diethylsulfamoyl-1,4-benzodioxane-5-carboxamide was produced (M.P.: 125° C.; yield 68%).

EXAMPLE 39

N-(1-benzyl-4-piperidyl)-7-methylsulfamoyl-1,4-benzodioxane-5-carboxamide 70 ml of water, 68.5 g of 7-methylsulfamoyl-1,4-benzodioxane-5-carboxylic acid, 25.5 g of triethylamine and 200 ml of acetone were introduced into a balloon flask provided with an agitator and a thermometer, and then 34.5 g of isobutyl chloroformiate was added, with the temperature being kept at from 15°–20° C. After the addition, at a temperature of from 15°–20° C., of 52 g of 1-benzyl-4-aminopiperidine and agitation of the mixture, the crystals formed were dried off, washed with water and then dried. The product formed was purified by treatment with a solution of hydrochloric acid and then precipitated by means of sodium hydroxide. The precipitate was then dried off, washed with water and dried. 76 g of N-(1-benzyl-4-piperidyl)-7-methylsulfamoyl-1,4-benzodioxane-5-carboxamide was produced (M.P.: 228° C.; yield: 68%).

EXAMPLE 40

N-(1-adamantyl)-1,4-benzodioxane-5-carboxamide 200 ml of chloroform and 37.5 g of adamantamine were introduced into a balloon flask provided with an agitator and a thermometer, and then 50 g of 1,4-benzodioxane-5-carbonyl chloride was added in portions at a temperature of from 5°–10° C. After agitation at abmient temperature 1500 ml of water was added and then chloroform was removed under vacuum. The base which was precipitated by ammonia was extracted by means of methylene chloride. After removal of the solvent the residue was dissolved in hydrochloric ethanol. The crystals formed by cooling were dried off, washed and then dried. 20 g of N-(1-adamantyl)-1,4-benzodioxane-5-carboxamide was produced (M.P.: 137° C.; yield: 25%).

EXAMPLE 41

N-(1-benzyl-2-pyrrolidylmethyl)-7-diethylsulfamoyl-1,4-benzodioxane-5-carboxamide phosphate 40 ml of water, 37.8 g of 7-diethylsulfamoyl-1,4-benzodioxane-5-carboxylic acid, 12.5 g of triethylamine and 120 ml of methyl ethyl ketone were introduced into a balloon flask provided with an agitator and a thermometer and then 17.2 g of isobutyl chloroformiate was added at a temperature of from 15°–20° C. After agitation of the mixture 25 g of 1-benzyl-2-aminomethylpyrrolidine was added, with the temperature being maintained at from 15°–20° C. The mixture was agitated at ambient temperature and then the solvents were removed. The residue was dissolved in 200 ml of methylene chloride and 300 ml of water. After agitation the solvent was decanted and then dried on magnesium sulfate. The solution was filtered and then the solvent removed. The resulting compound was dissolved in ethanol at boiling temperature and 18 g of 85% phosphoric acid was added. The crystals formed by cooling were dried off, washed with ice cold ethanol and then dried. 56 g of N-(1-benzyl-2-pyrrolidylmethyl)-7-diethylsulfamoyl-1,4-benzodioxane-5-carboxamide phosphate was produced (M.P.: 180° C.; yield 79.6%).

EXAMPLE 42

N-(1-benzyl-4-piperidyl)-1,4-benzodioxane-5-carboxamide hydrochloride 200 ml of chloroform and 50 g of 1-benzyl-4-amino piperidine were introduced into a balloon flask provided with an agitator and a thermometer, and then 50 g of 1,4-benzodioxane-5-carbonyl chloride was added in portions at a temperature of from 5°–10° C. After agitation of the mixture at ambient temperature the solvent was removed under vacuum and the residue was dissolved in 300 ml of water. After precipitation of the base by addition of ammonia, the water was removed and the resulting product was treated with a solution of hydrochloric acid. 75 g of N-(1-benzyl-4-piperidyl)-1,4-benzodioxane-5-carboxamide hydrochloride was produced (M.P.: 205° C.; yield: 77%).

EXAMPLE 43

N-(1-ethyl-2-pyrrolidylmethyl)-8-ethylsulfonyl-2H-3,4-dihydro-1,5-benzodioxepine-6-carboxamide hydrochloride 8-mercapto-2H-3,4-dihydro-1,5-benzodioxepine-6-carboxylic acid A solution of 106 g of 8-chlorosulfonyl-2H-3,4-dihydro-1,5-benzodioxepine-6-carboxylic acid in 273 ml of acetic acid and 159.5 g of tin were introduced into a balloon flask provided with an agitator and a thermometer. The mixture was agitated under heating at 40°–45° C. and then 705 ml of concentrated hydrochloric acid were added. After heating at 55°–60° C., the solution was cooled. The precipitate was dried off, washed and dried. 65 g of 8-mercapto-2H-3,4-dihydro-1,5-benzodioxepine-6-carboxylic acid were obtained (M.P.: 99.5°–100° C.; yield: 80%).

8-ethylthio-2H-3,4-dihydro-1,5-benzodioxepine-6-carboxylic acid 86 g of 8-mercapto-2H-3,4-dihydro-1,5-benzodioxepine-6-carboxylic acid, 152 ml of water, 76 ml of soda and 58.5 g of ethylsulfate were introduced into a balloon flask provided with a condenser. The mixture was heated under reflux and then cooled. 150 ml of water were added and then the solution was filtered and treated with 60 ml of hydrochloric acid. The precipitate was dried off, washed and dried. 88 g of 8-ethylthio-2H-3,4-dihydro-1,5-benzodioxepine-6-carboxylic acid were obtained (M.P.: 66°–67° C.; yield: 91%).

8-ethylsulfonyl-2H-3,4-dihydro-1,5-benzodioxepine-6-carboxylic acid 88 g of 8-ethylthio-2H-3,4-dihydro-1,5-benzodioxane-6-carboxylic acid in 528 ml of acetic acid were introduced into a balloon flask provided with a condenser and then 210 ml of hydrogen peroxide were added in portions. The solution was heated and the acetic acid removed under vacuum. The residue was dissolved in 180 ml of water and cooled. The precipitate was dried off, washed and dried. 90 g of 8-ethylsulfonyl-2H-3,4-dihydro-1,5-benzodioxepine-6-carboxylic acid were obtained (M.P.: 142°–143° C.; yield: 91%).

8-ethylsulfonyl-2H-3,4-dihydro-1,5-benzodioxepine-6-carbonyl chloride 75 g of thionyl chloride and 90 g of 8-ethylsulfonyl-2H-3,4-dihydro-1,5-benzodioxepine-6-carboxylic acid were introduced into a balloon flask provided with a condenser. The mixture was heated to 45°–50° C. and the thionyl chloride in excess was removed under vacuum. The residue was treated with petrolic ether and then dried off, washed and dried. 94 g of 8-ethylsulfonyl-2H-3,4-dihydro-1,5-benzodioxepine-6-carbonyl chloride were obtained (M.P.: 108°–110° C.; yield: 98%).

N-(1-ethyl-2-pyrrolidylmethyl)-8-ethylsulfonyl-2H-3,4-dihydro-1,5-benzodioxepine-6-carboxamide hydrochloride 39.5 g of 1-ethyl-2-aminomethylpyrrolidine in 282 ml of chloroform were introduced into a balloon flask provided with an agitator and a thermometer, and then 94 g of 8-ethylsulfonyl-2H-3,4-dihydro-1,5-benzodioxepine-6-carbonyl chloride were added in portions, the temperature being maintained at from 5°–10° C. The mixture was heated and then poured into water. The aqueous phase was cooled, filtered and treated with 30 ml of soda. The precipitate was extracted with methylene chloride and the organic phase was dried on potassium carbonate. The solvent was distilled off and the residue dissolved in isopropyl alcohol and treated with a solution of hydrochloric acid in isopropyl alcohol. The precipitate was dried off, washed with alcohol and dried. 98 g of N-(1-ethyl-2-pyrrolidylmethyl)-8-ethylsulfonyl-2H-3,4-dihydro-1,5-benzodioxepine-6-carboxamide hydrochloride were obtained (M.P.: 141°–142° C.; yield: 73%).

EXAMPLE 44

5-[(4-methyl-1-piperazinyl)-carbonyl]-6,7-dibromo-8-nitro-1,4-benzodioxane

6,7-dibromo-1,4-benzodioxane-5-carboxylic acid 1,440 ml of acetic acid and 360 g of 1,4-benzodioxane-5-carboxylic acid were introduced into a balloon flask provided with an agitator, an introduction funnel and a condenser. The mixture was heated to 55° C. and then a solution of 700 g of bromine in 360 ml of acetic acid was added in portions. The mixture was heated to 120° C. and then cooled to 15° C. The precipitate was dried off, washed with acetic acid and dried. 332 g of 6,7-dibromo-1,4-benzodioxane-5-carboxylic acid were obtained (M.P.: 212° C.). The structure was confirmed by nuclear magnetic resonance analysis.

6,7-dibromo-8-nitro-1,4-benzodioxane-5-carboxylic acid 166 g of 6,7-dibromo-1,4-benzodioxane-5-carboxylic acid and 500 ml of acetic acid were introduced into a balloon flask. The mixture was heated to 37° C. and then a solution of 60 ml of nitric acid (d=1.49) in 60 ml of acetic acid and sulfuric acid, as catalyst, were added. After heating to 50° C. the mixture was poured in cold water, under agitation. The precipitate was dried off, washed with water and dried. 107 g of 6,7-dibromo-8-nitro-1,4-benzodioxane-5-carboxylic acid were obtained (M.P.: 237° C.) The acid was purified by treatment with a solution of 50 g of sodium bicarbonate in 500 ml of water and precipitated with hydrochloric acid. The precipitate was dried off, washed and dried. Crystals were obtained (M.P. 238° C.; yield 61%). The structure was confirmed by nuclear magnetic resonance analysis.

6,7-dibromo-8-nitro-1,4-benzodioxane-5-carbonyl chloride 96 g of 6,7-dibromo-8-nitro-1,4-benzodioxane-5-carboxylic acid and 200 ml of thionyl chloride were introduced into a balloon flask provided with an agitator and a thermometer. The mixture was heated under reflux and then the excess thionyl chloride was removed under vacuum. The residue was dissolved in 100 ml of isopropyl ether and then the solvent removed and the product air-dried. 91 g of 6,7-dibromo-8-nitro-1,4-benzodioxane-5-carbonyl chloride were obtained (M.P.: 215° C.; yield: 91%).

5-[(4-methyl-1-piperazinyl)-carbonyl]-6,7-dibromo-8-nitro-1,4-benzodioxane 400 ml of methylethylcetone and 11 g of methylpiperazine were introduced into a balloon flask provided with an agitator and a thermometer. The mixture was cooled to 10° C. and then 41 g of 6,7-dibromo-8-nitro-1,4-benzodioxane-5-carbonyl chloride were added in portions with the temperature being maintained below 20° C. After agitation of the mixture, the crystals were dried off, washed with methylethylcetone and dried and then dissolved in water and reprecipitated by addition of 50 ml of 20% ammonia. The crystals were dried off, washed with water and dried. 33 g of 5-[(4-methyl-1-piperazinyl)-carbonyl]-6,7-dibromo-8-nitro-1,4-benzodioxane were obtained (M.P.: 164° C.; yield: 69.6%).

EXAMPLE 45

N-(1-ethyl-2-pyrrolidylmethyl)-6,7-dibromo-8-nitro-1,4-benzodioxane-5-carboxamide In a similar manner, by substituting 1-ethyl-2-aminomethylpyrrolidine for methylpiperazine, N-(1-ethyl-2-pyrrolidylmethyl)-6,7-dibromo-8-nitro-1,4-benzodioxane-5-carboxamide was obtained (M.P.: 2˙3° C.; yield: 65%). The structure was confirmed by nuclear magnetic research analysis.

EXAMPLE 46

N-(1-ethyl-2-pyrrolidylmethyl)-8-amino-1,4-benzodioxane-5-carboxamide

8-amino-1,4-benzodioxane-5-carboxylic acid 400 ml of water, 98.5 g of 6,7-dibromo-8-nitro-1,4-benzodioxane-5-carboxylic acid, 100 ml of soda and 10 g of Pd/c were introduced into an autoclave and then hydrogen under a pressure of 40 kg/cm$^2$ was introduced while heating to 50° C. The mixture was filtered and then treated with 95 ml of hydrochloric acid. The precipitate was dried off, washed and dried. 42 g of 8-amino-1,4-benzodioxane-5-carboxylic acid were obtained (M.P.: 186° C.; yield: 83.7%).

N-(1-ethyl-2-pyrrolidylmethyl)-8-amino-1,4-benzodioxane-5-carboxamide

According to the method described in Example 2, 42 g of 8-amino-1,4-benzodioxane-5-carboxylic acid were treated with methanol and the resulting compound treated with 33 g of 1-ethyl-2-aminomethylpyrrolidine and then with a solution of 13 g of hydrochloric acid in absolute alcohol. 49 g of N-(1-ethyl-2-pyrrolidylmethyl)-8-amino-1,4-benzodioxane-5-carboxamide dihydrochloride were obtained (M.P.: 173° C.; yield: 60%).

EXAMPLE 47

5-[(4-methyl-1-piperazinyl)-carbonyl]-8-chloro-1,4-benzodioxane

8-chloro-1,4-benzodioxane-5-carboxylic acid 29.3 g of 8-amino-1,4-benzodioxane-5-carboxylic acid, 120 ml of water and 30 ml of hydrochloric acid were introduced into a balloon flask provided with an agitator and a thermometer. The mixture was heated to 40° C. and then cooled to 5° C. and a solution of 10.5 g of sodium nitrite in 20 ml of water was added in portions with the temperature being maintained at from 5°-10° C. The mixture was agitated and then poured into a solution of 12 g of cuprous chloride in 45 ml of hydrochloric acid (d=1.18) with the temperature being maintained below 30° C. The precipitate was dried off, washed in 300 ml of water and 25 g of sodium bicarbonate. The solution was filtered and treated with hydrochloric acid. The precipitate was dried off, washed with water and dried. 20 g of 8-chloro-1,4-benzodioxane-5-carboxylic acid were obtained (M.P.: 195° C.; yield: 62%).

5-[(4-methyl-1-piperazinyl)-carbonyl]-8-chloro-1,4-benzodioxane

According to the method described in Example 33, 20 g of 8-chloro-1,4-benzodioxane-5-carboxylic acid were treated with thionyl chloride and the resulting 8-chloro-1,4-benzodioxane-5-carbonyl chloride (M.P.: 83° C.) was treated with 10.5 g of methylpiperazine. 14 g of 5-[(4-methyl-1-piperazinyl)-carbonyl]-8-chloro-1,4-benzodioxane were obtained (M.P.: 260° C. with decomposition; yield: 50.5%).

EXAMPLE 48

N-(1-ethyl-2-pyrrolidylmethyl)-8-acetamino-1,4-benzodioxane-5-carboxamide

8-acetamino-1,4-benzodioxane-5-carboxylic acid 43 g of 8-amino-1,4-benzodioxane-5-carboxylic acid and 72 ml of acetic acid were introduced into a balloon flask and then 24.5 ml of acetic anhydride were added in portions. The mixture was heated to 60°-70° C. and then cooled. The precipitate was dried off, washed with acetic acid and water and dried. 44 g of 8-acetamino-1,4-benzodioxane-5-carboxylic acid were obtained (M.P.: 233° C.; yield: 84%).

N-(1-ethyl-2-pyrrolidylmethyl)-8-acetamino-1,4-benzodioxane-5-carboxamide

According to the method described in Example 31, the 8-acetamino-1,4-benzodioxane-5-carboxylic acid was treated with isobutyl chloroformate and 1-ethyl-2-aminomethlpyrrolidine. N-(1-ethyl-2-pyrrolidylmethyl)-8-acetamino-1,4-benzodioxane-5-carboxamide was obtained. The structure was confirmed by nuclear magnetic resonance analysis.

EXAMPLE 49

N-(diethylaminoethyl)-7-nitro-8-acetamino-1,4-benzodioxane-5-carboxamide 42 g of 8-acetamino-1,4-benzodioxane-5-carboxylic acid, 75 ml of acetic acid and 75 ml of acetic anhydride were introduced into a balloon flask and then a solution of 17.5 ml of nitric acid (d=1.49) in 17 ml of acetic acid was added, with the temperature being left rising. After dissolution and crystallization, 50 ml of acetic acid were added. The mixture was agitated at 40°-45° C. and then cooled to 20° C. The precipitate was dried off, washed with acetic acid and water and dried. 13.5 g of a 50% mixture of 7-nitro-8-acetamino-1,4-benzodioxane-5-carboxylic acid and 6-nitro-8-acetamino-1,4-benzodioxane-5-carboxylic acid were obtained. The 7-nitro-8-acetamino-1,4-benzodioxane-5-carboxylic acid was separated and then treated according to the process of Example 31 with isobutyl chloroformate and diethylaminoethylamine. N-(diethylaminoethyl)-7-nitro-8-acetamino-1,4-benzodioxane-5-carboxamide was obtained. The structure was confirmed by nuclear magnetic resonance analysis.

EXAMPLE 50

N-(1-allyl-2-pyrrolidylmethyl)-7,8-azimido-1,4-benzodioxane-5-carboxamide

7,8-azimido-1,4-benzodioxane-5-carboxylic acid 13 g of a 50% mixture of 7-nitro-8-acetamino-1,4-benzodioxane-5-carboxylic acid and 6-nitro-8-acetamino-1,4-benzodioxane-5-carboxylic acid, 90 ml of water, 4.5 ml of sodium hydroxide, Raney nickel and hydrogene under a 50 kg/cm$^2$ pressure were introduced into an autoclave. At the end of the hydrogen absorption the nickel was filtered off and the solution was treated with 12 ml of hydrochloric acid and then with a solution of 3.5 g of sodium nitrite in 90 ml of water at a temperature of from 20°-25° C. The obtained precipitate was dried off, washed and then treated with an aqueous sodium hydroxyde solution. The mixture was acidified and then the precipitate was dried off, washed and dried. 3 g of 7,8-azimido-1,4-benzodioxane-5-carboxylic acid were obtained. (M.P: 260° C. with decomposition; yield: 59%).

N-(1-allyl-2-pyrrolidylmethyl)-7,8-azimido-1,4-benzodioxane-5-carboxamide

The 7,8-azimido-1,4-benzodioxane-5-carboxylic acid was treated with the N-hydroxyphthalimide together with the cicyclohexylcarbodiimide. The obtained phthalimide carboxylate was treated with the 1-allyl-2- aminomethylpyrrolidine. The N-(1-allyl-2-pyrrolidylmethyl)-7,8-azimido-1,4-benzodioxane-5-carboxamide was obtained, the structure of which was confirmed by nuclear magnetic resonance.

EXAMPLE 51

N-(2-pyrimidyl)-6-chloro-1,4-benzodioxane-5-carboxamide 6-nitro-1,4-benzodioxane-5-carboxylic acid 1,600 ml of acetic acid, 1,600 ml of acetic anhydride, and 1000 g of 1,4-benzodioxane-5-carboxylic acid were introduced in a 6-liter balloon flask provided with an agitator and a thermometer. The mixture was heated to 40° C. and a solution of 400 ml of nitric acid in 400 ml of acetic acid was added. After the introduction, the mixture was stirred at 40°-45° C. for two hours and then cooled to 5° C. The precipitate was dried off, washed with 600 ml of acetic acid and then with water and dried at 40° C. 700 g of 7-nitro-1,4-benzodioxane-5-carboxylic acid were collected, the structure of which was confirmed by nuclear magnetic resonance (M.P: 246° C.). The mother liquors were diluted with 25 liters of water and the obtained precipitate was dried off, washed with water and dried. 6-nitro-1,4-benzodioxane-5-carboxylic acid was obtained (M.P.: 188° C.).

6-amino-1,4-benzodioxane-5-carboxamide hydrochloride 195 g of 6-nitro-1,4-benzodioxane-5-carboxylic acid, 1950 ml of ethanol and some Raney nickel were introduced into an autoclave. The mixture was hydrogenated under a hydrogen pressure of 35 kg/cm$^2$ at 60° C. for one hour and then cooled. The nickel was filtered and the solution was acidified with 150 ml of an ethanolic solution of hydrochloric acid (23 g/100 ml). The precipitate was filtered and dried. 115 g of 6-amino-1,4-benzodioxane-5-carboxylic acid hydrochloride were obtained (M.P.: 160° C.; yield: 57.5%).

6-chloro-1,4-benzodioxane-5-carboxylic acid 58 g of 6-amino-1,4-benzodioxane-5-carboxylic acid hydrochloride and 116 ml of water were introduced in a 500 ml balloon flask provided with a stirrer, a thermometer and a dropping funnel. 28 ml of hydrochloric acid (d=1.18) were added and the mixture was cooled to a temperature of from 0°-5° C. A solution of 17.5 g of sodium nitrite in 38 ml of water was added at a temperature within the 0°-5° C. range. The mixture was stirred for one hour. 20 g of cuprous chloride and 75 ml of hydrochloric acid were added. The mixture was allowed to stand overnight and then filtered. The solid was washed with water, dried at 50° C. and purified by treatment with carbon black in alkaline solution (200 ml of water and 25 ml of 36° Be' caustic soda lye) and then 25 ml of hydrochloric acid was added. 40 g of 6-chloro-1,4-benzodioxane-5-carboxylic acid were obtained (M.P. 162° C.; yield: 74%).

6-chloro-1,4-benzodioxane-5-carbonyl chloride 56 ml of thionyl chloride, 28 g of 6-chloro-1,4-benzodioxane-5-carboxylic acid were introduced into a 250 ml balloon flask provided with a stirrer, a condenser and a thermometer. The mixture was heated at the reflux temperature for 30 minutes. The excess of thionyl chloride was removed by distillation under reduced pressure. 28.5 g of 6-chloro-1,4-benzodioxane-5-carbonyl chloride were obtained (M.P.: 50° C.; yield: 93%).

N-(2-pyrimidyl)-6-chloro-1,4-benzodioxane-5-carboxamide 280 ml of methyl ethyl ketone, 13 g of 2-aminopyrimidine were put into a 500 ml balloon flask provided with a stirrer and a thermometer. The mixture was cooled to 10° C. and 28 g of ground 6-chloro-1,4-benzodioxane-5-carbonyl chloride was added and stirred for two hours, the temperature being allowed to rise to 20° C. The obtained solid was filtered off, washed with 30 ml of methyl ethyl ketone and then dissolved in 250 ml of boiling water. The solution was treated with 10 ml of 36° Bel caustic soda lye. After filtration 12 g of product were obtained and crystallized again from 150 ml of ethanol. 9.5 g of N-(2-pyrimidyl)-6-chloro-1,4-benzodioxane-5-carboxamide was obtained. (M.P.: 223° C. with decomposition). The structure was confirmed by nuclear magnetic resonance analysis.

EXAMPLE 52

5-[(4-methyl-1-piperazinyl)-carbonyl)]6-nitro-1,4-benzodioxane hydrochloride 360 ml of methylethylcetone and 16 g of N-methylpiperazine were introduced into a 500 ml balloon flask provided with a stirrer and a thermometer. The mixture was cooled to 10° C. and then 36.5 g of 6-nitro-1,4-benzodioxane-5-carbonyl chloride were added in portions. The mixture was maintained under stirring at ambient temperature for one hour. The precipitate was dried off, washed with 150 ml of methylethylcetone, dried and then dissolved in 210 ml of cold water. The solution was acidified to a pH of 1 by addition of hydrochloric acid, treated with carbon black and filtered. The base was precipitated by addition of 15 ml of soda lye. The precipitate was washed with water and dried. 24 g were obtained (M.P.: 221° C.).

The base was then treated with 168 ml of ethanol containing 8 ml of water and 8 ml of hydrochloric acid (d=1.18). After crystallization the solid was filtered off, washed and dried. 19.5 g of 5[(4-methyl-1-piperazinyl)-carbonyl]-6-nitro-1,4-benzodioxane hydrochloride was obatined (M.P.: 205° C. with decomposition). The structure was confirmed by nuclear magnetic resonance analysis.

EXAMPLE 53

N-diethyl-7-cyclohexylsulfamoyl-1,4-benzodioxane-5-carboxamide 7-cyclohexylsulfamoyl-1,4-benzodioxane-5-carboxylic acid 250 ml of water and 300 ml of cyclohexylamine were put into a 1-liter balloon flask. 139 g of moist 7-chlorosulfonyl-1,4-benzodioxane-5-carboxylic acid were added by fractions, the temperature being maintained at from 20°-30° C. The mixture was stirred at room temperature for three hours and then the solution was treated with 30 g of black carbon 3S. After filtration, 300 ml of hydrochloric acid (d=1.18) were added. The precipitate was recrystallized, washed with water and dried. 92 g of 7-cyclohexylsulfamoyl-1,4-benzodioxane-5-carboxylic acid were obtained (M.P.: 150° C.).

N-diethyl-7-cyclohexylsulfamoyl-1,4-benzodioxane-6-carboxamide 34.1 g of 7-cyclohexylsulfamoyl-1,4-benzodioxane-5-carboxylic acid, 35 ml of water and 10.5 g of triethylamine were introduced into a 250 ml balloon flask provided with a stirrer and a thermometer. 100 ml of acetone were added and the mixture was cooled to 10° C. 14 g of isobutyl chloroformate were added and the mixture was maintained under stirring for 30 minutes at room temperature. 8 g of diethylamine were introduced at a temperature of from 15°-20° C. After stirring for three hours, the solvent was removed under vacuum. The residue was washed with water, dried, dissolved in 180 ml of absolute ethanol and treated with 3 g of black carbon. After filtration and crystallization, 23 g of diethyl-7-cyclohexylsulfamoyl-1,4-benzodioxane-5-carboxamide were obtained (M.P.: 201° C.). The structure was confirmed by infrared and nuclear magnetic resonance analyses.

EXAMPLE 54

N-(4-methyl-1-piperazinyl)-7-nitro-1,4-benzodioxane-5-carboxamide hydrochloride 7-nitro-1,4-benzodioxane-5-carbonyl chloride 112 ml of thionyl chloride, 56 g of 7-nitro-1,4-benzodioxane-5-carboxylic acid were introduced into a 250 ml balloon flask provided with a stirrer, a thermometer and a reflux condenser. The mixture was stirred and 1 ml of dimethylformamide was added with heating. After stirring for one hour at the reflux temperature, the excess of thionyl chloride was removed by distillation under vacuum. 61 g of 7-nitro-1,4-benzodioxane-5-carbonyl chloride were obtained (M.P.: 108° C.; yield: 100%).

N-(4-methyl-1-piperazinyl)-7-nitro-1,4-benzodioxane-5-carboxamide 33 g of 1-amino-4-methylpiperazine were dissolved in 630 ml of methyl ethyl ketone. The mixture was cooled to 10° C. and 61 g of 7-nitro-1,4-benzodioxane-5-carbonyl chloride were introduced by portions. The mixture was stirred for two hours and then the solid was filtered off and washed with 150 ml of methyl ethyl ketone. The obtained product was purified by transformation into the base (M.P.: 212° C.) and recrystallized by treatment with hydrochloric ethanol. 45 g of N-(4-methyl-1-piperazinyl)-7-nitro-1,4-benzodioxane-5-carboxamide were obtained (M.P.: 210° C. with one mole of water). The structure was confirmed by nuclear magnetic resonance and infrared analyses.

EXAMPLE 55

N-(1-allyl-2-pyrrolidylmethyl)-6,7-azimido-1,4-benzodioxane-5-carboxamide hydrochloride 1,4-benzodioxane-6,7-dinitro-5-carboxylic acid 165 ml of nitric acid (d=1.49) were put into a 500 ml balloon flask provided with a mechanical stirrer and a thermometer. 90 g of 1,4-benzodioxane-5-carboxylic acid were added at −10° C. The mixture was maintained for two hours at room temperature and then 1 liter of water was added. The precipitate was filtered off, washed with water, dried at 50° C. and then purified by recrystallization in acetic acid. 87 g of 1,4-benzodioxane-6,7-dinitro-5-carboxylic acid were collected (M.P.: 211° C.).

1,4-benzodioxane-6,7-diamino-5-carboxylic acid 135 g of 1,4-benzodioxane-6,7-dinitro-5-carboxylic acid, 500 ml of water and 50 ml of soda lye were introduced into a 1-liter autoclave and hydrogenated under a 80 kg pressure in the presence of Raney nickel. The mixture was heated to 100° C. for two hours and then cooled and filtered. The nickel was washed on the filter with 200 ml of water and the filtrates were kept all together. A sample was acidified with the hydrochloric acid to form the 1,4-benzodioxane-6,7-diamino-5-carboxylic acid dihydrochloride which was filtered, washed and dried. (M.P.: 153° C.).

1,4-benzodioxane-6,7-azimido-5-carboxylic acid

The above obtained filtrate was introduced into a two-liter balloon flask provided with a mechanical stirrer and a thermometer. A solution of 35 g of sodium nitrite in 70 ml of water was added dropwise at a temperature of from 20°-25° C. The crystallized product was filtered off, washed with water and dried at 50° C. 96 g of 1,4-benzodioxane-6,7-azimido-5-carboxylic acid was obtained (yield: 87%). The structure was confirmed by nuclear magnetic resonance analysis.

1,4-benzodioxane-6,7-azimido-5-N-phthalimide carboxylate 74 g of the 1,4-benzodioxane-6,7-azimido-5-carboxylic acid, 1 liter of dimethylformamide, 57 g of N-hydroxyphthalimide, 74.5 g of dicyclohexylcarbodiimide were heated at a temperature of 90° C. for 30 minutes. After cooling to 20° C., the crystals were filtered off and washed with 150 ml of dimethylformamide. The filtrates were evaporated under vacuum and the residue was treated with 400 ml of methanol. The solid was filtered, washed and dried. 80 g of 1,4-benzodioxane-6,7-azimido-5-N-phthalimide carboxylate were obtained (M.P.: above 250° C.; yield: 65.6%).

N-(1-allyl-2-pyrrolidylmethyl)-6,7-azimido-1,4-benzodioxane-5-carboxamide hydrochloride 92 g of 1,4-benzodioxane-6,7-azimido-5-N-phthalimide carboxylate, 500 ml of dimethylformamide were introduced into a 1-liter balloon flask provided with a mechanical stirrer and a thermometer. 45 g of 1-allyl-2-aminomethyl-pyrrolidine were added while stirring and were maintained at room temperature for two hours. After evaporation of the solvent, the residue was treated with 500 ml of hot acetone. After filtration, 50 ml of an ethanolic solution of hydrochloric acid were added to the filtrate. The product was filtered, washed and recrystallized. 50 g of N-(1-allyl-2-pyrrolidylmethyl)-6,7-azimido-1,4-benzodioxane-5-carboxamide hydrochloride were obtained (M.P.: 255° C.). The structure was confirmed by infrared and nuclear magnetic resonance analyses.

EXAMPLE 56

5-[(4-methyl-1-piperazinyl)-carbonyl]-6,7-dinitro-1,4-benzodioxane 1,4-benzodioxane-6,7-dinitro-5-N-phthalimide carboxylate 54 g of 1,4-benzodioxane-6,7-dinitro-5-carboxylic acid and 400 ml of dimethylformamide were introduced into a 1-liter balloon flask provided with a mechanical stirrer and a thermometer. 34.2 g of N-hydroxyphthalimide, 44.4 g of dicyclohexylcarbodiimide were added while stirring. The mixture was heated to 90° C. for 30 minutes and then cooled to 10° C. After filtration, the filtrate was reduced under vacuum and the residue recrystallized in the methanol. 67.5 g of 1,4-benzodioxane-6,7-dinitro-5-N-phthalimide carboxylate were obtained (M.P.: 225° C.; yield: 81.3%).

5[(4-methyl)-1-piperazinyl)-carbonyl]-6,7-dinitro-1,4-benzodioxane 67 g of 1,4-benzodioxane-6,7-dinitro-5-N-phthalimide carboxylate were dissolved in 400 ml of dimethylformamide. 20 g of N-methylpiperazine were added and the mixture was stirred for two hours. After evaporation of the solvent under vacuum, 1 liter of water was added to the residue. The solid was filtered and recrystallized in the dimethylformamide. 40 g of 5[(4-methyl)-1-piperazinyl)-carbonyl]-6,7-dinitro-1,4-benzodioxane were obtained (M.P.: 254° C.). The structure was confirmed by nuclear magnetic resonance analysis.

EXAMPLE 57

N-(1-piperidinopropyl)-6,7-diacetamino-1,4-benzodioxane-5-carboxamide

In the same manner as described in Example 53, the 6,7-diacetamino-1,4-benzodioxane-5-carboxylic acid (prepared by acetylation of the 6,7-diamino-1,4-benzodioxane-5-carboxylic acid) was condensed with the 1-piperidinopropylamine in the presence of the isobutyl chloroformiate. The N-(1-piperidinopropyl)-6,7-diacetamino-1,4-benzodioxane-5-carboxamide was obtained (M.P.: above 260° C. with decomposition). The structure was confirmed by nuclear magnetic resonance analysis.

EXAMPLE 58

5-[(4-methyl-1-piperazinyl)-carbonyl]-7-amino-1,4-benzodioxane

In the same manner as described in Example 2, the 7-amino-1,4-benzodioxane-5-carboxylic acid was treated with the methanol, and then the obtained carboxylic ester was reacted with N-methyl piperazine. 5[(4-methyl-1-piperazinyl)-carbonyl]-7-amino-1,4-benzodioxane was obtained (M.P.: 170° C.).

EXAMPLE 59

N-(1-ethyl-2-pyrrolidylmethyl)-1,4-benzodioxane-5-carboxamide hydrochloride

In the same manner as described in Example 17, by reaction of 1,4-benzodioxane-5-carbonyl chloride with the 1-ethyl-2-aminomethyl pyrrolidine, the N-(1-ethyl-2-pyrrolidylmethyl)-1,4-benzodioxane-5-carboxamide hydrochloride was obtained (M.P.: 149°–150° C.).

The compounds produced in the above examples are set forth in Table I.

TABLE I

| No Ex | X | Y | Z | A | NR' | B | $NR_1$ | $R_2$ |
|---|---|---|---|---|---|---|---|---|
| 1 | —H | $SO_2NHCH_3$ | H | —$(CH_2)_2$— | NH | —$CH_2$— | pyrrolidine N | $CH_2$—CH=$CH_2$ |
| 2 | H | $SO_2NH_2$ | H | —$(CH_2)_2$— | NH | —$CH_2$— | pyrrolidine N | $C_2H_5$ |
| 3 | H | $SO_2C_2H_5$ | H | —$(CH_2)_2$— | NH | —$CH_2$— | pyrrolidine N | $CH_3$ |
| 4 | H | $SO_2NH_2$ | H | —$(CH_2)_2$— | | —N(piperazine)N— | | —C(imidazole) |
| 5 | H | $SO_2N(CH_3)_2$ | H | —$(CH_2)_2$— | NH | —$CH_2$— | pyrrolidine N | $CH_3$ |
| 6 | H | H | H | —$(CH_2)_2$— | NH | —$CH_2$— | pyrrolidine N | —$CH_2$—C$_6$H$_5$ |
| 7 | H | $SO_2NH_2$ | H | —$(CH_2)_2$— | NH | —$CH_2$— | pyrrolidine N | $CH_2$—CH=$CH_2$ |
| 8 | H | $SO_2NHCH_3$ | H | —$(CH_2)_2$— | NH | —$CH_2$— | pyrrolidine N | $C_2H_5$ |

TABLE I-continued

| No Ex | X | Y | Z | A | NR' | B | NR₁ | R₂ |
|---|---|---|---|---|---|---|---|---|
| 9 | H | H | H | —(CH$_2$)— | NH | 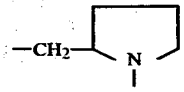 | | C$_2$H$_5$ |
| 10 (L) 11 (D) 12 (R) | H | SO$_2$C$_2$H$_5$ | H | —(CH$_2$)$_2$— | NH | 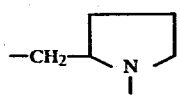 | | C$_2$H$_5$ |
| 13 | H | SO$_2$NH$_2$ | H | —(CH$_2$)$_2$— | NH | 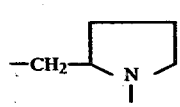 | | CH$_3$ |
| 14 | H | SO$_2$C$_2$H$_5$ | H | —(CH$_2$)$_2$— | NH | 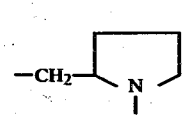 | | CH$_2$—CH=CH$_2$ |
| 15 | H | H | H | —(CH$_2$)$_3$— | NH |  | | C$_2$H$_5$ |
| 16 | H | SO$_2$NHCH$_3$ | H | —(CH$_2$)$_2$— | NH |  | | CH$_3$ |
| 17 | H | H | H | —(CH$_2$)$_2$— | NH | —CH$_2$—CH$_2$— | N—C$_2$H$_5$ | C$_2$H$_5$ |
| 18 | H | SO$_2$C$_2$H$_5$ | H | —(CH$_2$)$_2$— | NH | 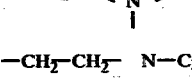 | | C$_2$H$_5$ |
| 19 | H | SO$_2$N(CH$_3$)$_2$ | H | —(CH$_2$)$_2$— | NH | 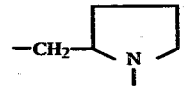 | | CH$_3$ |
| 20 | H | SO$_2$NHCH$_3$ | H | —(CH$_2$)$_2$— | NH | 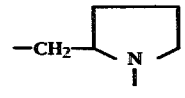 | | 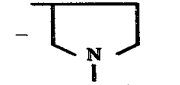 |
| 21 | H | SO$_2$N(CH$_3$)$_2$ | H | —(CH$_2$)$_2$— | NH |  | | C$_2$H$_5$ |
| 22 (D) 23 (L) | H | SO$_2$NHCH$_3$ | H | —(CH$_2$)$_2$— | NH | 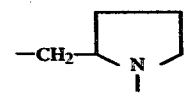 | | C$_2$H$_5$ |
| 24 (L) 25 (D) | H | SO$_2$NHCH$_3$ | H | —(CH$_2$)$_2$— | NH | 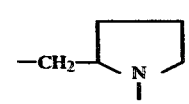 | | CH$_2$—CH=CH$_2$ |
| 26 (D) 27 (L) | H | SO$_2$NHCH$_3$ | H | —(CH$_2$)$_2$— | NH | 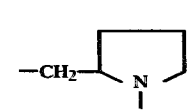 | | CH$_3$ |
| 28 | H | SO$_2$NHCH$_3$ | H | —(CH$_2$)$_3$— | NH |  | | C$_2$H$_5$ |

TABLE I-continued

| No Ex | X | Y | Z | A | NR' | B (R) | NR₁ | R₂ |
|---|---|---|---|---|---|---|---|---|
| 29 | H | H | H | −CH₂− | NH | | −CH₂−[pyrrolidine] | C₂H₅ |
| 30 | H | SO₂C₂H₅ | H | −(CH₂)₂− | | | [octahydropyrrolo[1,2-a]pyrazine] | |
| 31 | H | NO₂ | H | −(CH₂)₂− | | −N[piperazine]N− | | CH₃ |
| 32 | H | SO₂NH−[adamantyl] | H | −(CH₂)₂− | | −N[piperazine]N− | | CH₃ |
| 33 | H | Cl | H | −(CH₂)₂− | NH | −CH₂−CH₂− | | −N[piperidine] |
| 34 | H | SO₂NH−[adamantyl] | H | −(CH₂)₂− | N−(CH₂)₃CH₃ | | | H |
| 35 | OCH₃ | H | H | −(CH₂)₂− | NH | | −CH₂−[pyrrolidine] | C₂H₅ |
| 36 | OCH₃ | SO₂NH₂ | H | −(CH₂)₂− | NH | | −CH₂−[pyrrolidine] | C₂H₅ |
| 37 | H | H | H | −(CH₂)₂− | | | [octahydropyrrolo[1,2-a]pyrazine] | |
| 38 | H | SO₂N(C₂H₅)₂ | H | −(CH₂)₂− | −N−CH₂−[phenyl] | | | H |
| 39 | H | SO₃NHCH₃ | H | −(CH₂)₂− | NH | | [piperidine]N− | CH₂−[phenyl] |
| 40 | H | H | H | −(CH₂)₂− | N−[adamantyl] | | | H |
| 41 | H | SO₂N(C₂H₅)₂ | H | −(CH₂)₂− | NH | | −CH₂−[pyrrolidine] | CH₂−[phenyl] |
| 42 | H | H | H | −(CH₂)₂− | NH | | [piperidine]N− | CH₂−[phenyl] |
| 43 | H | SO₂C₂H₅ | H | −(CH₂)₃ | NH | | −CH₂−[pyrrolidine] | C₂H₅ |

TABLE I-continued

| No Ex | X | Y | Z | A | NR | B — NR₁ | R₂ |
|---|---|---|---|---|---|---|---|
| 44 | NO₂ | Br | Br | —(CH₂)₂— | | —N(piperazine)N— | CH₃ |
| 45 | NO₂ | Br | Br | —(CH₂)₂— | NH | —CH₂—(pyrrolidine) | C₂H₅ |
| 46 | NH₂ | H | H | —(CH₂)₂— | NH | —CH₂—(pyrrolidine) | C₂H₅ |
| 47 | Cl | H | H | —(CH₂)₂— | | —N(piperazine)N— | CH₃ |
| 48 | NHCOCH₃ | H | H | —(CH₂)₂— | NH | —CH₂—(pyrrolidine) | C₂H₅ |
| 49 | NHCOCH₃ | NO₂ | H | —(CH₂)₂— | NH | —CH₂—CH₂— N—C₂H₅ | C₂H₅ |
| 50 | | N=C(Cl)–N–NH (tetrazole) | H | —(CH₂)₂— | NH | —CH₂—(pyrrolidine) | CH₂—CH=CH₂ |
| 51 | H | H | Cl | —(CH₂)₂— | | —N—(pyrimidinyl) | H |
| 52 | H | H | NO₂ | —(CH₂)₂— | | —N(piperazine)N— | CH₃ |
| 53 | H | SO₂NH—(cyclohexyl) | H | —(CH₂)₂— | N—C₂H₅ | | C₂H₅ |
| 54 | H | NO₂ | H | —(CH₂)₂— | NH | —N(piperazine)N—CH₃ | |
| 55 | H | N=C(Cl)–N–NH (tetrazole) | | —(CH₂)₂— | NH | —CH₂—(pyrrolidine) | CH₂—CH=CH₂ |
| 56 | H | NO₂ | NO₂ | —(CH₂)₂— | | —N(piperazine)N— | CH₃ |
| 57 | H | NHCOCH₃ | NHCOCH₃ | —(CH₂)₂— | NH | —(CH₂)₃— | —N(piperidine) |
| 58 | H | NH₂ | H | —(CH₂)₂— | | —N(piperazine)N— | CH₃ |
| 59 | H | H | H | —(CH₂)₂ | NH | —CH₂—(pyrrolidine) | C₂H₅ |

The compounds of the present invention may be administered to patients in the form capsules, tablets, pills, granules, injectable solutions, etc., the preparation of which are well known. Additional substances that do not react with the compounds may be included, such as lactose, magnesium stearate, starch, talc, celluloses, levilite, alkali metal lauryl sulfates, saccharose and the usual vehicles used in medicinal preparations.

The compounds of the present invention may be administered to patients orally or parenterally in the daily dosage range of from about 50 to 900 mg. A more preferred range is about 50–300 mg per day, the most preferred daily dosage being about 100 to 150 mg per day.

The following examples are representative pharmaceutical preparations.

EXAMPLE 60

Tablets of the following composition were prepared:

|  | Form 1 | Form 2 | Form 3 |
|---|---|---|---|
| N-(1-ethyl-2-pyrrolidylmethyl)-7-methylsulfamoyl-1,4-benzoidioxane-5-carboxamide | 50 mg | 50 mg | 50 mg |
| Dried Starch | 30 mg | 30 mg | 20 mg |
| Lactose | 80 mg | 80 mg | 120 mg |
| Methylcellulose 1500 cps | 1.3 mg | 1.2 mg | 1.2 mg |
| Magnesium stearate | 3 mg | 2.5 mg | 3 mg |
| Levilite | 8 mg | 6.3 mg | 5.8 mg |

EXAMPLE 61

Tablets of the following composition were prepared:

| N-(1-methyl-2-pyrrolidylmethyl)-7-methylsulfamoyl-1,4-benzodioxane-5-carboxamide | 50 mg |
|---|---|
| Dried starch | 20 mg |
| Lactose | 80 mg |
| Methylcellulose 1500 cps | 1.3 mg |
| Levilite | 6 mg |
| Magnesium stearate | 3 mg |

EXAMPLE 62

Tablets of the following composition were prepared:

|  | Form 1 | Form 2 |
|---|---|---|
| N-(1-allyl-2-pyrrolidylmethyl)-7-methylsulfamoyl-1,4-benzodioxane-5-carboxamide | 50 mg | 50 mg |
| Dried starch | 15 mg | 10 mg |
| Lactose | 50 mg | 62 mg |
| Methylcellulose 1500 cps | 1 mg | 1 mg |
| Levilite | 5 mg | 5 mg |
| Magnesium stearate | 2 mg | 2 mg |

EXAMPLE 63

Tablets of the following composition were prepared:

| N-(1-methyl-2-pyrrolidylmethyl)-7-sulfamoyl-1,4-benzodioxane-5-carboxamide | 50 mg |
|---|---|
| Dried starch | 10 mg |
| Lactose | 50 mg |
| Methylcellulose | 0.94 mg |
| Levilite | 6 mg |
| Magnesium stearate | 2 mg |

EXAMPLE 64

Tablets of the following composition were prepared:

| N-(1-methyl-2-pyrrolidylmethyl)-7-ethylsulfonyl-1,4-benzodioxane-5-carboxamide | 50 mg |
|---|---|
| Dried starch | 10 mg |
| Lactose Codex | 50 mg |
| Methylcellulose 1500 cps | 0.55 mg |
| Levilite | 4 mg |
| Magnesium stearate | 2 mg |

EXAMPLE 65

Capsules of the following composition were prepared:

| N-(1-ethyl-2-pyrrolidylmethyl)-7-ethylsulfonyl-1-4,benzodioxane-5-carboxamide | 50 mg |
|---|---|
| Dried starch | 15 mg |
| Lactose | 50 mg |
| Methylcellulose 1500 cps | 1 mg |
| Levilite | 5 mg |
| Magnesium stearate | 2.5 mg |

Tablets may be prepared by mixing the selected compound with starch and lactose by the successive dilution method. The mixture is granulated with methylcellulose after which levilite, magnesium stearate and talc are added to the granulated mixture before being compressed to form the tablets. Though methylcellulose is commonly used as a granulating agent, other appropriate granulating agents may be used, as for example, ethyl cellulose, polyvinylpyrrolidone, starch paste, gum arabic, etc. Starch is used as a disintegrating agent, though alternate disintegrating agents include maize starch, carboxymethyl amyloids, alginates, microcrystalline cellulose, etc.

Injectable solutions may be prepared by dissolving a selected compound according to the invention in hydrochloric, levulinic, gluconic or glucoheptonic acid. The solution prepared under sterile conditions is made isotonic by an alkali metal chloride such as sodium chloride, after which preservatives are added. Alternatively, the injectable solutions may be prepared without adding preservatives; the ampoule is filled under nitrogen and sterilized for one-half hour at 100° C.

The compounds of the present invention have been found to have very low toxicity which is entirely compatible with therapeutic use without danger of secondary effects. The acute toxicity of the compounds were studied in the Swiss mouse with both parenteral (intravenous, intra-peritoneal and subcutaneous) and oral administration. The results of the studies in the mouse are given in the following Table II wherein the numbering of the compounds corresponds to the numbers of the examples.

TABLE II

| Compound | TOXICITY DL 50 - Mice - mg/kg (base) | | | |
|---|---|---|---|---|
| | IV | IP | SC | PO |
| 1 | 171,5–172 | 522–540 | 1344–1440 | |
| 2 | 48–49,6 | 312–320 | 594–624 | 0% at 3000 mg/kg |
| 3 | 120–120,4 | | | |
| 5 | 220,8–225,6 | | | |
| 7 | 96,6–100 | | | |
| 8 | 84,6–90 | 322–328 | 1450–1485 | 35% at 2000 mg/kg |
| 10 | 150–157,5 | 350–363 | | 1260–1360 |
| 11 | 168–184 | 442–450 | | |
| 12 | 147–154 | 480 | 1225–1230 | 1400–1470 |
| 13 | 64–67,5 | 234–240 | 430–437 | 0% at 3000 mg/kg |
| 14 | 146–157 | 325–338 | 420–442 | 2900–3491 |
| 15 | 96,7–86.2 | 224–227 | 572–613 | 756 |
| 16 | 88–96 | 380–396 | 925–1014 | 2760–2900 |
| 17 | 49,1 | 241 | 575 | 544–679 |
| 20 | 72,5–76 | 180–184,5 | 476–499,4 | 1190–1200 |
| 21 | 196–208 | | | |
| 22 | 83,6–86 | | | |
| 23 | 115,5–126 | | | |
| 24 | 216–232 | | | |
| 25 | 160–168 | | | |
| 26 | 105–116 | | | |
| 27 | 80–83,6 | | | |
| 28 | 141–154 | 387,5–418 | 1620–1850 | 2100–2400 |
| 39 | 164–175 | 896–957 | 960 | 1560–1600 |

The compounds of the present invention are moreover virtually devoid of cataloeptic activity. The compounds are administered subcutaneously to rats. The criterion for the cataleptic state was the immobility of the animal for 30 seconds with its front limbs apart and arranged carefully on cubes of wood 4 cm high, thus placing the animal in an unaccustomed and uncomfortable position. The cataleptic action was measured with the effect of the administered compound at its maximum. The results are given in the following Table III wherein the numbering of the compounds corresponds to the numbers of the examples.

TABLE III

| Compound | CATALEPTIC ACTIVITY DE 50 SC - Rat - mg/kg |
|---|---|
| 1 | Effect of 40% at 200 mg/kg |
| 2 | Inactive....at 200 mg/kg |
| 3 | 325 |
| 4 | Effect of 30% at 20 mg/kg |
| 7 | Inactive....at 200 mg/kg |
| 8 | Effect of 10% at 200 mg/kg |
| 10 | Inactive....at 200 mg/kg |
| 11 | Inactive....at 200 mg/kg |
| 12 | Inactive....at 200 mg/kg |
| 13 | Inactive....at 200 mg/kg |
| 14 | Effect of 10% at 200 mg/kg |
| 15 | Inactive....at 200 mg/kg |
| 16 | Inactive....at 200 mg/kg |
| 17 | 389 |
| 20 | Inactive....at 200 mg/kg |
| 21 | Inactive....at 200 mg/kg |
| 24 | Effect of 30% at 200 mg/kg |
| 25 | Inactive....at 200 mg/kg |
| 28 | Inactive....at 200 mg/kg |
| 39 | Inactive....at 200 mg/kg |

From these results it will be seen that the compounds of the present invention are virtually devoid of cataleptic activity in rats. This property permits clinical usage of the compounds with a high degree of tolerance with respect to the extrapyramidal system.

The compounds of the present invention were also found to be particularly active in dogs with respect to the central emetic agents such as apomorphine. In this instance the experimental procedure followed was that of CHEN and ENSOR. The compounds of the invention were administered subcutaneously 30 minutes before apomorphine (100 µg/kg/SC). The animal was observed one-half hour after the injection of the alkaloid. The results are given in Table IV wherein the numbering of the compounds corresponds to the numbers of the examples.

TABLE IV:

| Compound | ANTIEMETIC ACTIVITY DE 50 µg/kg/SC - Dog |
|---|---|
| 1 | 3 |
| 2 | Effect of 8% at 5 µg/kg/SC |
| 3 | 5.5 |
| 5 | 10 |
| 8 | 1.5 |
| 10 | 2 |
| 11 | 40 |
| 12 | 3.5 |
| 13 | 9 |
| 14 | 3.9 |
| 15 | 30 |
| 16 | 2.3 |
| 20 | 3.5 |
| 21 | 4 |

The results of the experiments carried out on laboratory animals justified tests with the compounds of the invention in human medicine. The following examples demonstrate the effectiveness of the compounds.

EXAMPLE 66

A patient 38 year old suffering from Hodgkins Disease had been subjected to repeated chemotherapy as an out-patient once a week. Each session was accompanied by nausea followed by substantial vomiting, persisting for 24 hours in spite of the usual treatment.

Treatment of the patient, 24 hours before the beginning of the perfusion and 4 hours afterwards, with 50 mg of N-(1-ethyl-2-pyrrolidylmethyl)-7-methylsulfamoyl-1,4-benzodioxane-5 carboxamide totally suppressed the nausea and vomiting attacks. The medication was well tolerated and no secondary affect was observed.

EXAMPLE 67

A 28-year old data processing engineer suffered from a characterial neurosis with bouts of anxiety culminating in three attempts at suicide. Analytical treatment for 18 months made it possible to achieve social reintegration but had little affect on the anxiety aspect.

The administration of 50 mg of N-(1-methyl-2-pyrrolidylmethyl)-7-methylsulfamoyl-1,4-benzodioxane-5-carboxamide three times per day caused in a few days the complete disappearance of any anxiety, without any sedative action. The medication was well tolerated, and no secondary affect was observed.

EXAMPLE 68

A patient 78 years old had been suffering for 8 months from severe reactional depression. The existence of a prostatic adenoma prevented the use of tricyclics.

The patient was treated three times per day with 50 mg of N-(1-methyl-Z-pyrrolidylmethyl)-7-methylsulfamoyl-1,4-benzodioxane-5-carboxamide. Within three weeks his condition had substantially improved, and he was permitted to leave the hospital. The treatment was continued at home for three months making it possible for the patient to maintain an excellent psychic balance with the resumption of normal activity for a retired person of this age. The medication was well tolerated, and no secondary affect was observed.

EXAMPLE 69

A 42-year old patient underwent a hysterectomy for a fibroid tumor. about six months previously. Following the operation, hot flushes (10 to 20 per day) appeared with attacks of sweating which awoke the patient during the night and caused her to be embarrassed while at work.

The patient was treated with N-(1-ethyl-2-pyrrolidylmethyl)-7-methylsulfamoyl-1,4-benzodioxane-5-carboxamide at a single dose of 100 mg per day. The symptoms disappeared within four days with only one hot flush occurring every two or three days during the daytime. The medication was well tolerated and no side-effects were observed.

EXAMPLE 70

A 47-year old patient suffered, following menopause, from repeated attacks of cystitis with frequent and severe urgency such that no social life was possible. The patient consulted both general practitioners and specialists. All tests were negative and all treatment was without affect in this classical case of cystitis.

The patient was treated for some days with N-(1-methyl-2-pyrrolidylmethyl)-7-methylsulfamoyl-1,4-benzodioxane-5-carboxamide at a dose of 150 mg per day. The symptoms completely disappeared and her psychological state became normal.

What is claimed is:

1. Substituted 2,3-alkylene bis(oxy)benzamides, their pharmaceutically acceptable acid addition salts, their quaternary ammonium salts, their oxides, and their dextrorotatory and levorotatory isomers, having the formula:

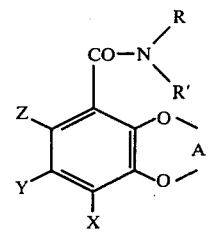

wherein

A is a $C_{1-3}$ alkylene group;

X is selected from the group consisting of hydrogen, halogen, $C_{1-4}$ alkoxy, nitro, amino, and acetamino, and when X is alkoxy A is not methylene;

Y is selected from the group consisting of hydrogen, halogen, nitro, amino, acetamino, $C_{1-4}$ alkylsulfonyl, sulfamoyl, $C_{1-4}$ alkylsulfamoyl, and $C_{1-4}$ dialkylsulfamoyl;

Z is selected from the group consisting of hydrogen, nitro, amino, and acetamino;

R is a group having the formula:

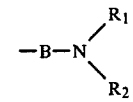

wherein

B is a $C_{1-3}$ alkylene group;

$R_1$ is joined to B to form a pyrrolidinyl group;

$R_2$ is a $C_{1-4}$ alkyl, $C_{2-4}$ alkenyl, cycloalkyl or benzyl group; and

R' is a hydrogen atom, a $C_{1-4}$ alkyl, adamantyl or benzyl group.

2. The benzamide of claim 1 wherein X is selected from the group consisting of methoxy, ethoxy, propoxy, isopropoxy, butoxy, isobutoxy and t-butoxy.

3. The benzamide of claim 1 wherein Y is selected from the group consisting of methylsulfonyl, ethylsulfonyl, propylsulfonyl, isopropylsulfonyl, butylsulfonyl, isobutylsulfonyl and t-butylsulfonyl.

4. The benzamide of claim 1 wherein said $C_{1-4}$ alkyl of said $R_2$ is selected from the group consisting of methyl, ethyl, propyl, isopropyl, butyl, isobutyl and t-butyl.

5. The benzamide of claim 1 wherein said $C_{2-4}$ alkenyl of said $R_2$ is selected from the group consisting of vinyl and allyl.

6. The benzamide of claim 1 wherein R' is selected from the group consisting of methyl, ethyl, propyl, isopropyl, butyl, isobutyl and t-butyl.

7. The benzamide of claim 1 wherein R is a 1-alkyl-2-pyrrolidylalkyl group.

8. The benzamide of claim 1 wherein R is a 1-ethyl-2-pyrrolidylmethyl group.

9. The benzamide of claim 1 wherein R is a 1-methyl-2-pyrrolidylmethyl group.

10. The benzamide of claim 1 wherein R is a 1-cycloalkyl-3-pyrrolidyl group.

11. The benzamide of claim 1 wherein R is a 1-cyclohexyl-3-pyrrolidyl group.

12. The benzamide of claim 1 wherein R is a 1-alkenyl-2-pyrrolidylalkyl group.

13. The benzamide of claim 1 wherein R is a 1-allyl-2-pyrrolidylmethyl group.

14. The benzamide of claim 1 wherein said compound is N-(1-allyl-2-pyrrolidylmethyl)-7-methylsulfamoyl-1,4-benzodioxane-5-carboxamide.

15. The benzamide of claim 1 wherein said compound is N-(1-ethyl-2-pyrrolidylmethyl)-7-sulfamoyl-1,4-benzodioxane-5-carboxamide.

16. The benzamide of claim 1 wherein said compound is N-(1-methyl-2-pyrrolidylmethyl)-7-ethylsulfonyl-1,4-benzodioxane-5-carboxamide.

17. The benzamide of claim 1 wherein said compound is N-(1-methyl-2-pyrrolidylmethyl)-7-dimethylsulfamoyl-1,4-benzodioxane-5-carboxamide.

18. The benzamide of claim 1 wherein said compound is N-(1-benzyl-2-pyrrolidylmethyl)-1,4-benzodioxane-5-carboxamide.

19. The benzamide of claim 1 wherein said compound is N-(1-allyl-2-pyrrolidylmethyl)-7-sulfamoyl-1,4-benzodioxane-5-carboxamide.

20. The benzamide of claim 1 wherein said compound is N-(1-ethyl-2-pyrrolidylmethyl)-7-methylsulfamoyl-1,4-benzodioxane-5-carboxamide.

21. The benzamide of claim 1 wherein said compound is N-(1-ethyl-2-pyrrolidylmethyl)-2,3-methylenedioxy benzamide.

22. The benzamide of claim 1 wherein said compound is N-(1-ethyl-2-pyrrolidylmethyl)-7-ethylsulfonyl-1,4-benzodioxane-5-carboxamide.

23. The benzamide of claim 1 wherein said compound is N-(1-methyl-2-pyrrolidylmethyl)-7-sulfamoyl-1,4-benzodioxane-5-carboxamide.

24. The benzamide of claim 1 wherein said compound is N-(1-allyl-2-pyrrolidylmethyl)-7-ethylsulfonyl-1,4-benzodioxane-5-carboxamide.

25. The benzamide of claim 1 wherein said compound is N-(1-ethyl-2-pyrrolidylmethyl)-2H-3,4-dihydro-1,5-benzodioxepine-6-carboxamide.

26. The benzamide of claim 1 wherein said compound is N-(1-methyl-2-pyrrolidylmethyl)-7-methylsulfamoyl-1,4-benzodioxane-5-carboxamide.

27. The benzamide of claim 1 wherein said compound is N-(1-cyclohexyl-3-pyrrolidyl)-7-methylsulfamoyl-1,4-benzodioxane-5-carboxamide.

28. The benzamide of claim 1 wherein said compound is N-(1-ethyl-2-pyrrolidylmethyl)-7-dimethylsulfamoyl-1,4-benzodioxane-5-carboxamide.

29. The benzamide of claim 1 wherein said compound is N-(1-ethyl-2-pyrrolidylmethyl)-8-methylsulfamoyl-2H-3,4-dihydro-1,5-benzodioxepine-6-carboxamide.

30. The benzamide of claim 1 wherein said compound is N-(1-ethyl-2-pyrrolidylmethyl)-8-methoxy-1,4-benzodioxane-5-carboxamide.

31. The benzamide of claim 1 wherein said compound is N-(1-ethyl-2-pyrrolidylmethyl)-8-methoxy-7-sulfamoyl-1,4-benzodioxane-5-carboxamide.

32. The benzamide of claim 1 wherein said compound is N-(1-benzyl-2-pyrrolidylmethyl)-7-diethylsulfamoyl-1,4-benzodioxane-5-carboxamide.

33. The benzamide of claim 1 wherein said compound is N-(1-ethyl-2-pyrrolidylmethyl)-8-ethylsulfonyl-2H-3,4-dihydro-1,5-benzodioxepine-6-carboxamide.

34. The benzamide of claim 1 wherein said compound is N-(1-ethyl-2-pyrrolidylmethyl)-6,7-dibromo-8-nitro-1,4-benzodioxane-5-carboxamide.

35. The benzamide of claim 1 wherein said compound is N-(1-ethyl-2-pyrrolidylmethyl)-8-amino-1,4-benzodioxane-5-carboxamide.

36. The benzamide of claim 1 wherein said compound is N-(1-ethyl-2-pyrrolidylmethyl)-1,4-benzodioxane-5-carboxamide.

* * * * *